United States Patent
Grubbs et al.

(10) Patent No.: US 6,759,537 B2
(45) Date of Patent: Jul. 6, 2004

(54) HEXACOORDINATED RUTHENIUM OR OSMIUM METAL CARBENE METATHESIS CATALYSTS

(75) Inventors: Robert H. Grubbs, South Pasadena, CA (US); Jennifer A. Love, Pasadena, CA (US); Melanie S. Sanford, Plainsboro, NY (US); Tina M. Trnka, Pasadena, CA (US); Jason L. Moore, Huntsville, TX (US)

(73) Assignees: California Institute of Technology, Pasadena, CA (US); Cymetech, LLP, Huntsville, TX (US)

( * ) Notice: Subject to any disclaimer, the term of this patent is extended or adjusted under 35 U.S.C. 154(b) by 0 days.

(21) Appl. No.: 10/017,489

(22) Filed: Dec. 14, 2001

(65) Prior Publication Data

US 2002/0177710 A1 Nov. 28, 2002

Related U.S. Application Data

(63) Continuation-in-part of application No. 09/948,115, filed on Sep. 5, 2001, now Pat. No. 6,610,626.
(60) Provisional application No. 60/314,978, filed on Aug. 24, 2001, provisional application No. 60/278,311, filed on Mar. 23, 2001, provisional application No. 60/288,680, filed on May 3, 2001, and provisional application No. 60/309,806, filed on Aug. 1, 2001.

(51) Int. Cl.[7] .......................... C07D 227/06; B01J 31/24
(52) U.S. Cl. ...................... 548/101; 548/262.2; 556/22; 556/136; 502/155; 502/167; 526/171; 526/172
(58) Field of Search .............................. 548/101, 262.2; 556/136, 22; 502/155; 526/171, 172, 167

(56) References Cited

U.S. PATENT DOCUMENTS 5,342,909 A    8/1994  Grubbs et al. .............. 526/171

(List continued on next page.)

FOREIGN PATENT DOCUMENTS

JP           270892 A   10/2001    ........... C07F/15/00

(List continued on next page.)

OTHER PUBLICATIONS

Grubbs, et al. "Ring–Closing Metathesis and Related Pro- (List continued on next page.)

Primary Examiner—Robert Harlan
(74) Attorney, Agent, or Firm—David Jaffer; Pillsbury Winthrop LLP

(57) ABSTRACT

The present invention relates to novel hexacoordinated metathesis catalysts and to methods for making and using the same. The inventive catalysts are of the formula

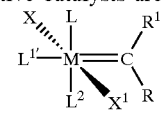

wherein:
M is ruthenium or osmium;
X and $X^1$ are the same or different and are each independently an anionic ligand;
L, $L^{1'}$ and $L^2$ are the same or different and are each independently a neutral electron donor ligand, wherein at least one L, $L^{1'}$ and $L^2$ is an N-heterocyclic carbene ligand; and,
R and $R^1$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the R or $R^1$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

26 Claims, 2 Drawing Sheets

U.S. PATENT DOCUMENTS

Figure 1:
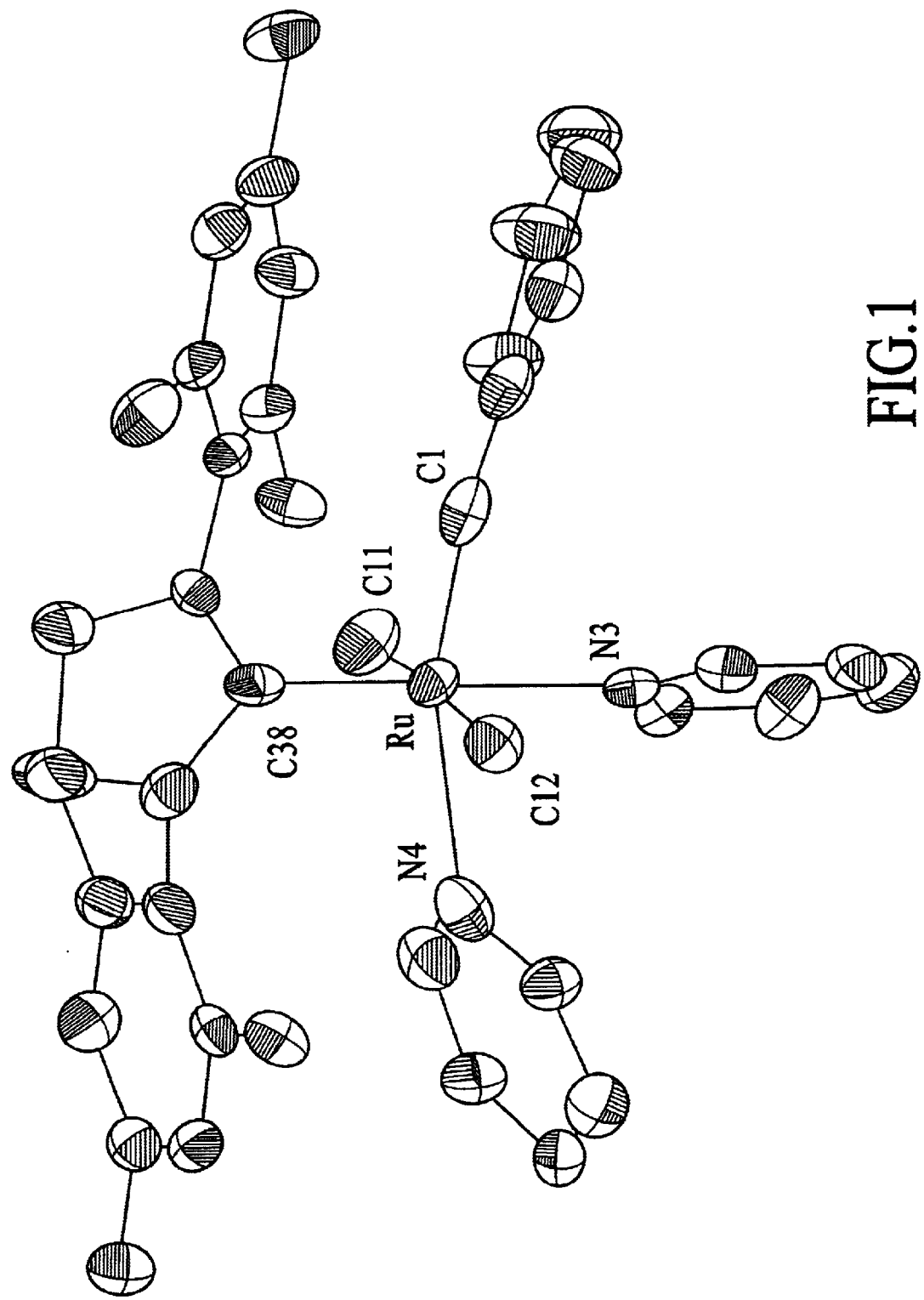

| | | | |
|---|---|---|---|
| 5,710,298 A | 1/1998 | Grubbs et al. | 556/22 |
| 5,728,785 A | 3/1998 | Grubbs et al. | 526/142 |
| 5,728,917 A | 3/1998 | Grubbs et al. | 585/653 |
| 5,750,815 A | 5/1998 | Grubbs et al. | 585/511 |
| 5,831,108 A | 11/1998 | Grubbs et al. | 556/21 |
| 6,077,805 A * | 6/2000 | Van Der Schaaf et al. | 502/155 |

FOREIGN PATENT DOCUMENTS

| | | | |
|---|---|---|---|
| WO | WO15339 | 3/2000 | B01J/31/00 |
| WO | WO39346 | 6/2000 | |
| WO | WO39346 | 6/2000 | B01J/31/22 |

OTHER PUBLICATIONS cesses in Organic Synthesis" Acc. Chem. Res. 1995, 28, pp 446–452.

Nguyen, et al. "Synthesis and Activities of New SingleComponent, Ruthenium–Based Olefin Metathesis Catalysts" Journal of the American Chemical Society, 1993, 115, pp. 9858–9859.

Le Bozec, et al "A New Route To Vinylcarbene Metal Complexes in One Step from 2–Propyn–1–ols and Arene Ruthenium(II) Derivaties" Journal Chemical Society, Chem. Commun. 1989, pp 219–221.

Dias, et al. "Well–Defined Ruthenium Olefin Metathesis Catalysts: Mechanism and Activity" Journal American Chemical Society 1997, 119, pp 3887–3897.

* cited by examiner

HEXACOORDINATED RUTHENIUM OR OSMIUM METAL CARBENE METATHESIS CATALYSTS

This application claims the benefit of U.S. Provisional Patent Application No. 60/314,978 filed Aug. 24, 2001 U.S. Provisional Application No. 60/278,311 filed Mar. 23, 2001 U.S. Provisional Application No. 60/288,680 filed May 3, 2001 U.S. Provisional Application No. 60/309,806 filed Aug. 1, 2001, and is a continuation-in-part of U.S. patent application Ser. No. 09/948,115, filed Sep. 5, 2001 now U.S. Pat. No. 6,610,626, the contents of each of which are incorporated herein by reference.

The U.S. Government has certain rights in this invention pursuant to Grant No. CHE-9809856 awarded by the National Science Foundation and Grant No. GM31322 awarded by the National Institute of Health.

BACKGROUND

Metathesis catalysts have been previously described by for example, U.S. Pat. Nos. 5,312,940, 5,342,909, 5,728,917, 5,750,815, 5,710,298, and 5,831,108 and PCT Publications WO 97/20865 and WO 97/29135 which are all incorporated herein by reference. These publications describe well-defined single component ruthenium or osmium catalysts that possess several advantageous properties. For example, these catalysts are tolerant to a variety of functional groups and generally are more active than previously known metathesis catalysts. Recently, the inclusion of an N-heterocyclic carbene (NHC) ligand, such as an imidazolidine or triazolylidene ligand as described in U.S. application Ser. Nos. 09/539,840, 09/576,370 and PCT Publication No. WO 99/51344, the contents of each of which are incorporated herein by reference, in these metal-carbene complexes has been found to improve the already advantageous properties of these catalysts. In an unexpected and surprising result, the shift in structure from the well-established penta-coordinated catalyst structure to the hexa-coordinated catalyst structure has been found to significantly improve the properties of the catalyst. For example, these hexacoordinated catalysts of the present invention exhibit increased activity and selectivity not only in ring closing metathesis ("RCM") reactions, but also in other metathesis reactions including cross metathesis ("CM") reactions, reactions of acyclic olefins, and ring opening metathesis polymerization ("ROMP") reactions.

SUMMARY

The present invention relates to novel hexacoordinated metathesis catalysts and to methods for making and using the same. The inventive catalysts are of the formula

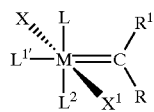

wherein:
  M is ruthenium or osmium;
  X and $X^1$ are the same or different and are each independently an anionic ligand;
  L, $L^{1'}$ and $L^2$ are the same or different and are each independently a neutral electron donor ligand, wherein at least one L, $L^{1'}$ and $L^2$ is an N-heterocyclic carbene ligand; and, R and $R^1$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the R or $R^1$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In preferred embodiments, $L^2$ and $L^{1'}$ are pyridine and L is a phosphine or an N-heterocyclic carbene ligand. Examples of N-heterocyclic carbene ligands include:

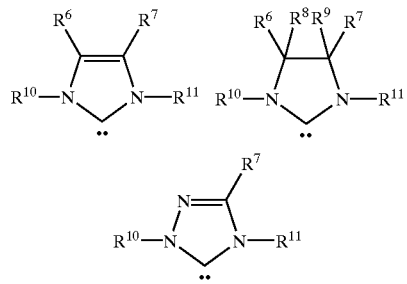

wherein R, $R^1$ $R^6$, $R^7$, $R^8$, $R^9$, $R^{10}$ and $R^{11}$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the R, $R^1$ $R^6$, $R^7$, $R^8$, $R^9$, $R^{10}$ and $R^{11}$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. The inclusion of an NHC ligand to the hexacoordinated ruthenium or osmium catalysts has been found to dramatically improve the properties of these complexes. Because the NHC-based hexacoordinated complexes are extremely active, the amount of catalysts that is required is significantly reduced.

DETAILED DESCRIPTION OF THE PREFERRED EMBODIMENTS

The present invention generally relates to ruthenium and osmium carbene catalysts for use in olefin metathesis reactions. More particularly, the present invention relates to hexacoordinated ruthenium and osmium carbene catalysts and to methods for making and using the same. The terms "catalyst" and "complex" herein are used interchangeably.

Unmodified ruthenium and osmium carbene complexes have been described in U.S. Pat. Nos. 5,312,940, 5,342,909, 5,728,917, 5,750,815, and 5,710,298, all of which are incorporated herein by reference. The ruthenium and osmium carbene complexes disclosed in these patents all possess metal centers that are formally in the +2 oxidation state, have an electron count of 16, and are penta-coordinated. These catalysts are of the general formula

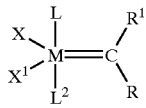

wherein:

M is ruthenium or osmium;

X and $X^1$ are each independently any anionic ligand;

L and $L^1$ are each independently any neutral electron donor ligand;

R and $R^1$ are the same or different and are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the R or $R^1$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

The catalysts of the present invention are similar in that they are Ru or Os complexes; however, in these complexes, the metal is formally in the +2 oxidation state, and has an electron count of 18 and are hexacoordinated. These catalysts are of the general formula:

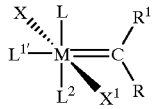

wherein

M is ruthenium or osmium;

X and $X^1$ are the same or different and are each independently any anionic ligand;

L, $L^{1'}$, and $L^2$ are the same or different and are each independently any neutral electron donor ligand;

R and $R^1$ are the same or different and are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the R or $R^1$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

The hexacoordinated complex provides several advantages over the well-known pentacoordinated complexes. For example, the hexacoordinated complexes have greater air stability in the solid state because they are coordinatively saturated. Due to the lability of the additional ligand, e.g. pyridines, the complexes initiate faster than the phosphine based pentacoordinated species. Slow initiation means that only a small amount of complex is actually catalytically active thereby wasting much of the added complex. With faster initiators, catalyst loading is lowered. Further, and without being bound by theory, it is believed that the slower propogation of the hexacoordinated complexes, due to the re-binding of the labile ligands relative to the phosphines, translates to lower polydisperity. Moreover, the coordinatively saturated species crystallize better than their pentacoordinated counterparts. In addition, due to the lability of the ligands in the hexacoordinated complexes (e.g. pyridines and chlorines), these complexes allow access to previously inaccessible complexes and provide with higher purity certain complexes that can be obtained through different routes. For example, the pentacoordinated benzylidene with triphenylphosphine as its phosphine ligand can be prepared in higher yield and with greater purity using the hexacoordinated complex. The pentacoordinated benzylidene with P(p-$CF_3C_6H_4)_3$ as its phosphine ligand is inaccessible through existing routes. Without being bound by theory, it is believe that this is because it would require the substitution of a stronger donor ligand with a weaker donor ligand. Substitution of the anionic ligands of the hexacoordinated complexes is much more rapid than with the corresponding pentacoordinated species (e.g. phosphine bound). Without being bound by theory, it is believed that this results from the requirement of ligand dissociation before anionic ligand substitution. Thus complexes with fast dissociation of their neutral electron donor ligands will undergo faster substitution.

The catalysts of the invention are also useful for ring-opening metathesis polymerization (ROMP), ring-closing metathesis (RCM), ADMET, and cross-metathesis. The synthesis and polymerization of olefins via these metathesis reactions can be found in, for example, U.S. application Ser. No. 09/891,144 entitled: "Synthesis of Functionalized and Unfunctionalized Olefins, filed Jun. 25, 2001, and U.S. application Ser. No. 09/491,800, now U.S. Pat. No. 6,306,988 the contents of each of which are incorporated herein by reference. Preferred embodiments of the catalysts of the invention possess at least one NHC ligand attached to the metal center, as illustrated by the following general formula:

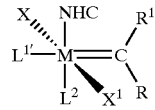

In preferred embodiments of the inventive catalysts, the R substituent is hydrogen and the $R^1$ substituent is selected from the group consisting of $C_1$–$C_{20}$ alkyl, $C_2$–$C_{20}$ alkenyl, and aryl. In even more preferred embodiments, the $R^1$ substituent is phenyl or vinyl, optionally substituted with one or more moieties selected from the group consisting of $C_1$–$C_5$ alkyl, $C_1$–$C_5$ alkoxy, phenyl, and a functional group. In especially preferred embodiments, $R^1$ is phenyl or vinyl substituted with one or more moieties selected from the group consisting of chloride, bromide, iodide, fluoride, —$NO_2$, —$NMe_2$, methyl, methoxy and phenyl. In the most preferred embodiments, the $R^1$ substituent is phenyl or —C=C(CH$_3$)$_2$. When $R^1$ is vinyl, the catalyst is of the general formula:

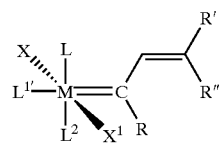

wherein M, L, $L^1$, $L^{1'}$, $L^2$, X, $X^1$, and R are as defined above. R' and R" are preferably independently hydrogen or phenyl but can be selected from any of the groups listed for R or $R^1$.

In preferred embodiments of the inventive catalysts, X and $X^1$ are each independently hydrogen, halide, or one of the following groups: $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, or $C_1$–$C_{20}$ alkylsulfinyl. Optionally, X and $X^1$ may be substituted with one or more moieties selected from the group consisting of $C_1$–$C_{10}$ alkyl, $C_1$–$C_{10}$ alkoxy, and aryl which in turn may each be further substituted with one or more groups selected from halogen, $C_1$–$C_5$ alkyl, $C_1$–$C_5$ alkoxy, and phenyl. In more preferred embodiments, X and $X^1$ are halide, benzoate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate. In even more preferred embodiments, X and $X^1$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, X and $X^1$ are each chloride.

L, $L^1$, $L^{1'}$ and $L^2$ may be any appropriate monodentate or multidentate neutral electron donor ligands. Multidentate neutral electron donor ligands include bidentate, tridentate, or tetradentate neutral electron donor ligands, for example. In preferred embodiments of the inventive catalysts, L, $L^1$, $L^{1'}$ and $L^2$ are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether, or any derivatives therefrom. At least one L, $L^1$, $L^{1'}$ and $L^2$ may also be an N-heterocyclic carbene ligand. Preferred embodiments include complexes where both $L^{1'}$ and $L^2$ are either the same or different NHC ligands.

In preferred embodiments, at least one of L, $L^1$, $L^{1'}$ and $L^2$ is a phosphine of the formula $PR^3R^4R^5$, where $R^3$, $R^4$, and $R^5$ are each independently aryl or $C_1$–$C_{10}$ alkyl, particularly primary alkyl, secondary alkyl or cycloalkyl. In the even more preferred embodiments, at least one of L, $L^1$, $L^{1'}$ and $L^2$ is each selected from the group consisting of —P(cyclohexyl)$_3$, —P(cyclopentyl)$_3$, —P(isopropyl)$_3$, and —P(phenyl)$_3$. Even more preferably, at least one of L, $L^1$, $L^{1'}$ and $L^2$ is an NHC ligand. A preferred embodiment include where L is an NHC, $L^1$ is P(cyclohexyl)$_3$ or —P(cyclopentyl)$_3$, and $L^{1'}$ and $L^2$ are each heterocyclic ligands, optionally aromatic, or together form a bidenatate ligand. Preferably $L^{1'}$ and $L^2$ are each independently pyridine or a pyridine derivative.

Examples of NHC ligands include ligands of the general formulas:

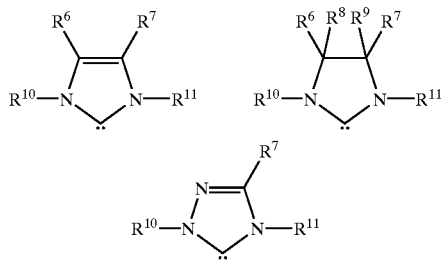

wherein R, $R^1$, R', R", $R^6$, $R^7$, $R^8$, $R^9$, $R^{10}$, and $R^{11}$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the R, $R^1$ $R^6$, $R^7$, $R^8$, $R^9$, $R^{10}$, and $R^{11}$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In preferred embodiments, $R^6$, $R^7$, $R^8$ and $R^9$ are independently selected from the group consisting of hydrogen, phenyl, or together form a cycloalkyl or an aryl optionally substituted with one or more moieties selected from the group consisting of $C_1$–$C_{10}$ alkyl, $C_1$–$C_{10}$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen; and $R^{10}$ and $R^{11}$ are each is independently $C_1$–$C_{10}$ alkyl or aryl optionally substituted with $C_1$–$C_5$ alkyl, $C_1$–$C_5$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In more preferred embodiments, $R^6$ and $R^7$ are both hydrogen or phenyl, or $R^6$ and $R^7$ together form a cycloalkyl group; $R^8$ and $R^9$ are hydrogen and $R^{10}$ and $R^{11}$ are each either substituted or unsubstituted aryl. Without being bound by theory, it is believed that bulkier $R^{10}$ and $R^{11}$ groups result in catalysts with improved characteristics such as thermal stability. In especially preferred embodiments, $R^{10}$ and $R^{11}$ are the same and each is independently of the formula:

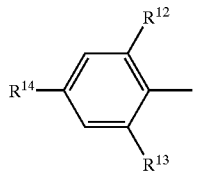

wherein:

R[12], R[13], and R[14] are each independently hydrogen, $C_1-C_{10}$ alkyl, $C_1-C_{10}$ alkoxy, aryl, or a functional group selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. In especially preferred embodiments, R[12], R[13], and R[14] are each independently selected from the group consisting of hydrogen, methyl, ethyl, propyl, isopropyl, hydroxyl, and halogen. In the most preferred embodiments, R[12], R[13], and R[14] are the same and are each methyl.

In these complexes, R[6], R[7], R[8], and R[9] are each independently hydrogen or a substituent selected from the group consisting of $C_1-C_{20}$ alkyl, $C_2-C_{20}$ alkenyl, $C_2-C_{20}$ alkynyl, aryl, $C_1-C_{20}$ carboxylate, $C_1-C_{20}$ alkoxy, $C_2-C_{20}$ alkenyloxy, $C_2-C_{20}$ alkynyloxy, aryloxy, $C_2-C_{20}$ alkoxycarbonyl, $C_1-C_{20}$ alkylthio, $C_1-C_{20}$ alkylsulfonyl and $C_1-C_{20}$ alkylsulfinyl. Iimidazolidine ligands are also referred to as imidizol-2-ylidene ligands.

Other examples of neutral electron donor ligands include ligands which are derived, for example, from unsubstituted or substituted heteroarenes such as furan, thiophene, pyrrole, pyridine, bipyridine, picolylimine, gamma-pyran, gamma-thiopyran, phenanthroline, pyrimidine, bipyrimidine, pyrazine, indole, coumarone, thionaphthene, carbazole, dibenzofuran, dibenzothiophene, pyrazole, imidazole, benzimidazole, oxazole, thiazole, dithiazole, isoxazole, isothiazole, quinoline, bisquinoline, isoquinoline, bisisoquinoline, acridine, chromene, phenazine, phenoxazine, phenothiazine, triazine, thianthrene, purine, bisimidazole and bisoxazole.

Examples of substituents are OH, halogen, $C(O)OR_{s1}$, $OC(O)R_{s4}$, $C(O)R_{s2}$, nitro, $NH_2$, cyano, $SO_3M_y$, $OSO_3M_y$, $NR_{20}SO_3M_y$, N=N—$R_{s2}$, $C_1-C_{12}$ alkyl, $C_2-C_{12}$ alkenyl, $C_1-C_{12}$ alkoxy, $C_3-C_{12}$ cycloalkyl, $C_3-C_{12}$ cycloalkenyl, $C_{12}-C_{11}$ heterocycloalkyl, $C_2-C_{11}$ heterocycloalkenyl, $C_6-C_{10}$ aryl, $C_6-C_{10}$ aryloxy, $C_5-C_9$ heteroaryl, $C_5-C_9$ heteroaryloxy, $C_7-C_{11}$ aralkyl, $C_7-C_{11}$ aralkyloxy, $C_6-C_{10}$ heteroaralkyl, $C_8-C_{11}$ aralkenyl, $C_7-C_{10}$ heteroaralkenyl, monoamino, diamino, sulfonyl, sulfonamide, carbamide, carbamate, sulfohydrazide, carbohydrazide, carbohydroxamic acid residue and aminocarbonylamide, in which $R_{s1}$ is hydrogen, $M_y$, $C_1-C_{12}$ alkyl, $C_2-C_{12}$ alkenyl, $C_3-C_{12}$ cycloalkyl, $C_2-C_{11}$ heterocycloalkyl, $C_6-C_{10}$ aryl, $C_5-C_9$ heteroaryl, $C_7-C_{11}$ aralkyl or $C_6-C_{10}$ heteroaralkyl, $R_{s4}$ is hydrogen, $C_1-C_{12}$ alkyl, $C_2-C_{12}$ alkenyl, $C_3-C_{12}$ cycloalkyl, $C_2-C_{11}$ heterocycloalkyl, $C_{16}-C_{10}$ aryl, $C_5-C_{19}$ heteroaryl, $C_7-C_{11}$ aralkyl or $C_6-C_{10}$ heteroaralkyl, and $R_{s2}$ and $R_{s20}$ are hydrogen, $C_1-C_{12}$ alkyl, $C_2-C_{12}$ alkenyl, $C_3-C_{12}$ cycloalkyl, $C_3-C_{12}$ cycloalkenyl, $C_2-C_{11}$ heterocycloalkyl, $C_1-C_{11}$ heterocycloalkenyl, $C_6-C_{10}$ aryl, $C_5-C_9$ heteroaryl, $C_7-C_{11}$ aralkyl, $C_6-C_{10}$ heteroaralkyl, $C_8-C_{11}$ aralkenyl or $C_7-C_{10}$ heteroaralkenyl, and alkyl, alkenyl, alkoxy, cycloalkyl, cycloalkenyl, heterocycloalkyl, heterocycloalkenyl, aryl, aryloxy, heteroaryl, heteroaryloxy, aralkyl, aralkyloxy, heteroaralkyl, aralkenyl and heteroaralkenyl in turn are unsubstituted or substituted by one of the above-mentioned substituents; and y is 1 and M is a monovalent metal or y is ½ and M is a divalent metal.

In the context of the description of the present invention, the terms metal and corresponding cations refer to an alkali metal, for example Li, Na or K, an alkaline earth metal, for example Mg, Ca or Sr, or Mn, Fe, Zn or Ag, and corresponding cations. Lithium, sodium and potassium ions, with their salts, are preferred. $NH_2$, monoamino, diamino, carbamide, carbamate, carbohydrazide, sulfonamide, sulfohydrazide and aminocarbonylamide correspond preferably to a group $R_8$ $C(O)(NH)_pN(R_9)$—, —$C(O)(NH)_pNR_8R_9$, $R_8OC(O)(NH)_pN(R_9)$—, $R_8R_{40}NC(O)(NH)_pN(R_9)$—, —$OC(O)(NH)_pNR_8R_9$, —$N(R_{40})C(O)(NH)_pNR_8R_9$, $R_8S(O)_2(NH)_pN(R_9)$—; —$S(O)_2(NH)_pNR_8R_9$; $R_8R_{40}NS(O)_2N(R_9)$—or —$NR_{40}S(O)_2NR_8R_9$, in which $R_8$, $R_9$ and $R_{40}$ independently of one another are hydrogen, OH, $C_1-C_{12}$ alkyl, $C_1-C_{12}$ alkenyl, $C_3-C_{12}$ cycloalkyl, $C_3-C_{12}$ cycloalkenyl, $C_2-C_{11}$ heterocycloalkyl, $C_2-C_{11}$ heterocycloalkenyl, $C_6-C_{10}$ aryl, $C_5-C_9$ heteroaryl, $C_7-C_{16}$ aralkyl, $C_8-C_{16}$ aralkenyl with $C_2-C_6$ alkenylene and $C_6-C_{10}$ aryl, $C_6-C_{15}$ heteroaralkyl, $C_6-C_{15}$ heteroaralkenyl, or di-$C_6-C_{10}$ aryl-$C_1-C_6$ alkyl, or $R_8'R_9'N$, in which $R_8'$ and $R_9'$ independently of one another are hydrogen, OH, $SO_3M_y$, $OSO_3M_y$, $C_1-C_{12}$ alkyl, $C_3-C_{12}$ cycloalkyl, $C_2-C_{11}$ heterocycloalkyl, $C_6-C_{10}$ aryl, $C_5-C_9$ heteroaryl, $C_7-C_{11}$ aralkyl, $C_6-C_{10}$ heteroaralkyl, $C_8-C_{16}$ aralkenyl with $C_2-C_6$ alkenylene and $C_6-C_{10}$ aryl, or di-$C_6-C_{10}$ aryl-$C_1-C_6$ alkyl, which are unsubstituted or substituted by one or more substituents from the group consisting of OH, halogen, $C(O)OR_{s1}$, $OC(O)R_{s4}$, $C(O)R_{s2}$, nitro, $NH_2$, cyano, $SO_3Z_y$, $OSO_3Z_y$, $NR_{20}SO_3Z_y$, $C_1-C_{12}$ alkyl, $C_2-C_{12}$ alkenyl, $C_1-C_{12}$ alkoxy, $C_3-C_{12}$ cycloalkyl, $C_3-C_{12}$ cycloalkenyl, $C_2-C_{11}$ heterocycloalkyl, $C_2-C_{11}$ heterocycloalkenyl, $C_6-C_{10}$ aryl, $C_6-C_{10}$ aryloxy, $C_5-C_9$ heteroaryl, $C_5-C_9$ heteroaryloxy, $C_7-C_{11}$ aralkyl, $C_7-C_{11}$ aralkyloxy, $C_6-C_{10}$ heteroaralkyl, $C_8-C_{11}$ aralkenyl, $C_7-C_{10}$ heteroaralkenyl, monoamino, diamino, sulfonyl, sulfonamide, carbamide, carbamate, sulfohydrazide, carbohydrazide, carbohydroxamic acid residue and aminocarbonylamide, in which $R_{s1}$ is hydrogen, $Z_y$, $C_1-C_{12}$ alkyl, $C_2-C_{12}$ alkenyl, $C_3-C_{12}$ cycloalkyl, $C_2-C_{11}$ heterocycloalkyl, $C_6-C_{10}$ aryl, $C_5-C_9$ heteroaryl, $C_7-C_{11}$ aralkyl or $C_6-C_{10}$ heteroaralkyl, $R_{s4}$ is hydrogen, $C_1-C_{12}$ alkyl, $C_2-C_{12}$ alkenyl, $C_3-C_{12}$ cycloalkyl, $C_2-C_{11}$ heterocycloalkyl, $C_6-C_{10}$ aryl, $C_5-C_9$ heteroaryl, $C_7-C_{11}$ aralkyl or $C_6-C_{10}$ heteroaralkyl, and $R_{s2}$ is hydrogen $C_1-C_{12}$ alkyl, $C_2-C_{12}$ alkenyl, $C_3-C_{12}$ cycloalkyl, $C_3-C_{12}$ cycloalkenyl, $C_2-C_{11}$ heterocycloalkyl, $C_2-C_{11}$ heterocycloalkenyl, $C_6-C_{10}$ aryl, $C_5-C_9$ heteroaryl, $C_7-C_{11}$ aralkyl, $C_6-C_{10}$ heteroaralkyl, $C_8-C_{11}$ aralkenyl or $C_7-C_{10}$ heteroaralkenyl, and alkyl, alkenyl, alkoxy, cycloalkyl, cycloalkenyl, heterocycloalkyl, heterocycloalkenyl, aryl, aryloxy, heteroaryl, heteroaryloxy, aralkyl, aralkyloxy, heteroaralkyl, aralkenyl and heteroaralkenyl in turn are unsubstituted or substituted by one of the above-mentioned substituents; p is 0 or 1 and y is 1 and Z is a monovalent metal or y is ½ and Z is a divalent metal; or $R_8$ and $R_9$ or $R_{8'}$ and $R_{9'}$ or $R_8$ and $R_{40}$ in the case of —$NR_8R_9$ or —$NR_{8'}R_{9'}$ or $R_8R_{40}N$— together are tetramethylene, pentamethylene, —$(CH_2)_2$—O—$(CH_2)_2$—, —$(CH_2)_2$—S—$(CH_2)_2$— or —$(CH_2)_2$—$NR_7$—$(CH_2)_2$—, and $R_7$ is H, $C_1-C_6$ alkyl, $C_7-C_{11}$ aralkyl, $C(O)R_{s2}$ or sulfonyl.

The sulfonyl substituent is, for example, of the formula $R_{10}$—$SO_2$— in which $R_{10}$ is $C_1-C_{12}$ alkyl, $C_3-C_{12}$ cycloalkyl, $C_2-C_{11}$ heterocycloalkyl, $C_6-C_{10}$ aryl, $C_5-C_9$ heteroaryl, $C_7-C_{11}$ aralkyl or $C_6-C_{10}$ heteroaralkyl which are unsubstituted or substituted by one or more substituents selected from the group consisting of OH, halogen, C(O)OR$_{s1}$, OC(O)R$_{s4}$, C(O)R$_{s2}$, nitro, NH$_2$, cyano, SO$_3$Z$_y$, OSO$_3$Z$_y$, NR$_{20}$SO$_3$Z$_y$, C$_1$–C$_{12}$ alkyl, C$_2$–C$_{12}$ alkenyl, C$_1$–C$_{12}$ alkoxy, C$_3$–C$_{12}$ cycloalkyl, C$_3$–C$_{12}$ cycloalkenyl, C$_2$–C$_{11}$ heterocycloalkyl, C$_2$–C$_{11}$ heterocycloalkenyl, C$_6$–C$_{10}$ aryl, C$_6$–C$_{10}$ aryloxy, C$_5$–C$_9$ heteroaryl, C$_5$–C$_9$ heteroaryloxy, C$_7$–C$_{10}$ aralkyl, C$_6$–C$_{10}$ heteroaralkyl, C$_8$–C$_{11}$ aralkenyl, C$_7$–C$_{10}$ heteroaralkenyl, monoamino, diamino, sulfonyl, sulfonamide, carbamide, carbamate, sulfonhydrazide, carbohydrazide, carbohydroxamic acid residue and aminocarbonylamide, in which R$_{s1}$ is hydrogen, Z$_y$, C$_1$–C$_{12}$ alkyl, C$_2$–C$_{12}$ alkenyl, C$_3$–C$_{12}$ cycloalkyl, C$_2$–C$_{11}$ heterocycloalkyl, C$_6$–C$_{10}$ aryl, C$_5$–C$_9$ heteroaryl, C$_7$–C$_{11}$ aralkyl or C$_6$–C$_{10}$ heteroaralkyl, R$_{s4}$ is hydrogen, C$_1$–C$_{12}$ alkyl, C$_2$–C$_{12}$ alkenyl, C$_3$–C$_{12}$ cycloalkyl, C$_2$–C$_{11}$ heterocycloalkyl, C$_6$–C$_{10}$ aryl, C$_5$–C$_9$ heteroaryl, C$_7$–C$_{11}$ aralkyl or C$_6$–C$_{10}$ heteroaralkyl, and R$_{s2}$ and R$_{20}$ are hydrogen, C$_1$–C$_{12}$ alkyl, C$_2$–C$_{12}$ alkenyl, C$_3$–C$_{12}$ cycloalkyl, C$_3$–C$_{12}$ cycloalkenyl, C$_2$–C$_{11}$ heterocycloalkyl, C$_2$–C$_{11}$ heterocycloalkenyl, C$_6$–C$_{10}$ aryl, C$_5$–C$_9$ heteroaryl, C$_7$–C$_{11}$ aralkyl, C$_6$–C$_{10}$ heteroaralkyl, C$_8$–C$_{11}$ aralkenyl or C$_7$–C$_{10}$ heteroaralkenyl, and alkyl, alkenyl, alkoxy, cycloalkyl, cycloalkenyl, heterocycloalkyl, heterocycloalkenyl, aryl, aryloxy, heteroaryl, heteroaryloxy, aralkyl, heteroaralkyl, aralkenyl and heteroaralkenyl in turn are unsubstituted or substituted by one of the above-mentioned substituents; and y is 1 and Z is a monovalent metal or y is ½ and Z is a divalent metal. Preferred neutral electron donor ligands are derived, for example, from heteroarenes of the group

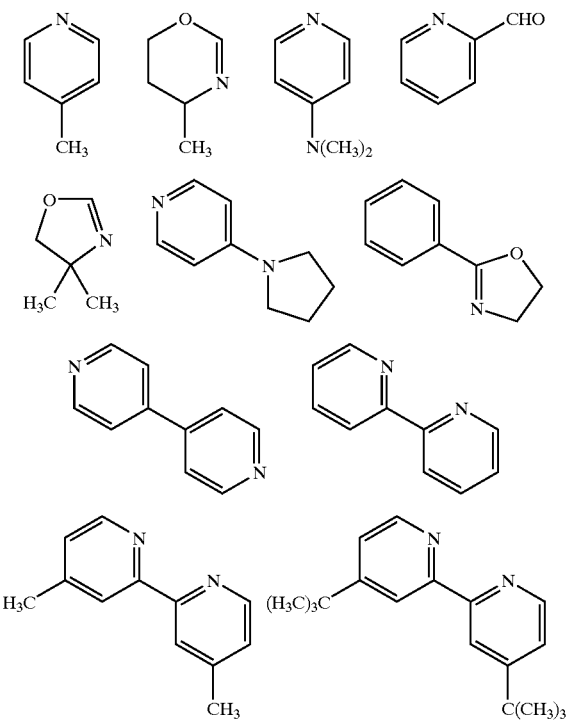

-continued

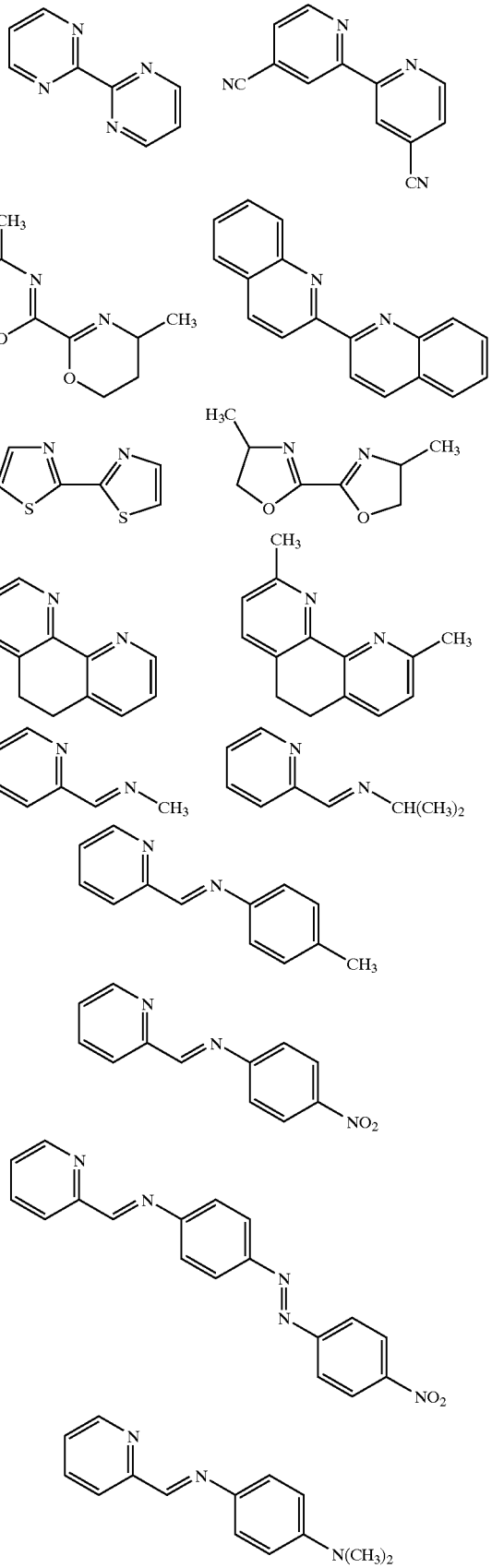

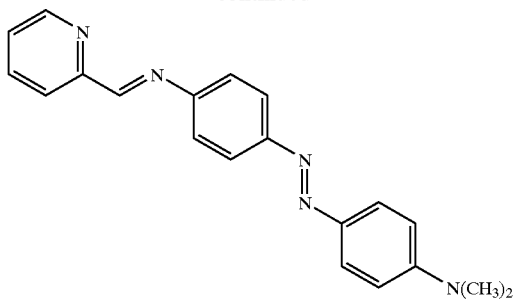

A more preferred group of compounds is formed when $L^2$ and $L^{1'}$ independently of one another are pyridyl which is unsubstituted or substituted by one or more substituents from the group consisting Of $C_1$–$C_{12}$ alkyl, $C_2$–$C_{11}$ heterocycloalkyl, $C_5$–$C_9$ heteroaryl, halogen, monoamino, diamino and —C(O)H. Examples are

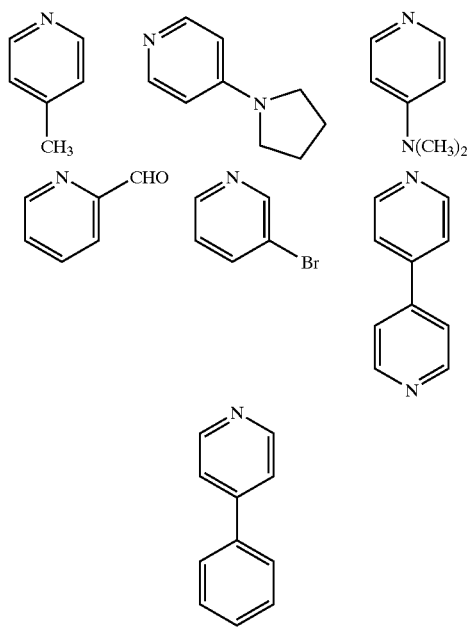

Another preferred group of compounds is formed when $L^2$ and $L^{1'}$ together are bipyridyl, phenanthrolinyl, bithiazolyl, bipyrimidinyl or picolylimine which are unsubstituted or substituted by one or more sub stituents from the group consisting of $C_1$–$C_{12}$ alkyl, $C_6$–$C_{10}$ aryl and cyano, the substituents alkyl and aryl being in turn unsubstituted or substituted by one or more substituents from the group consisting of $C_1$–$C_{12}$ alkyl, nitro, monoamino, diamino and nitro- or diamino-substituted —N=.N—$C_6$–$C_{10}$ aryl. Examples are:

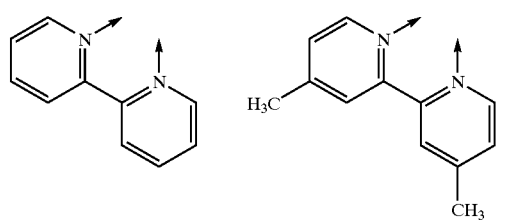

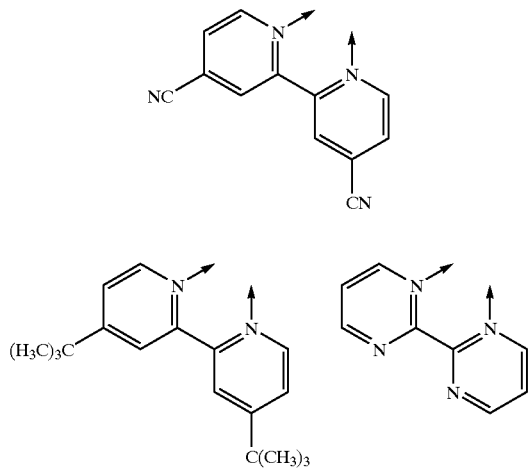

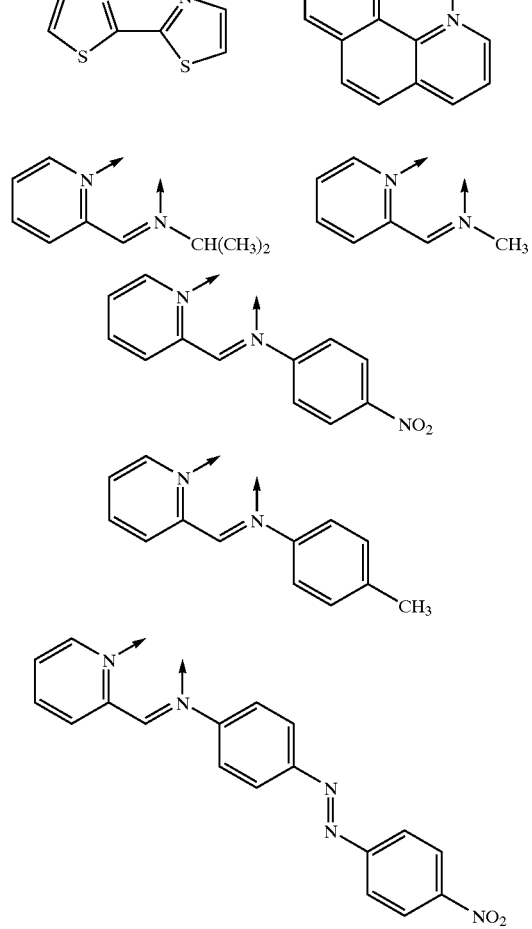

13

-continued

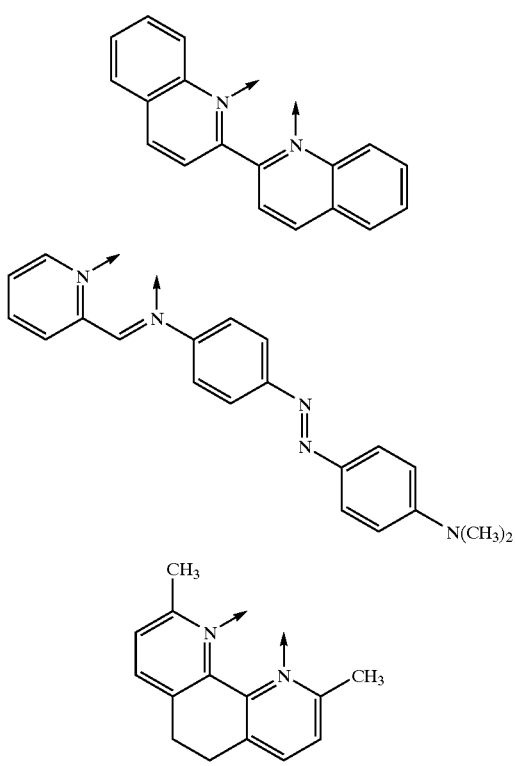

Even more preferably, $L^2$ and $L^{1'}$ are each independently selected from the group consisting of:

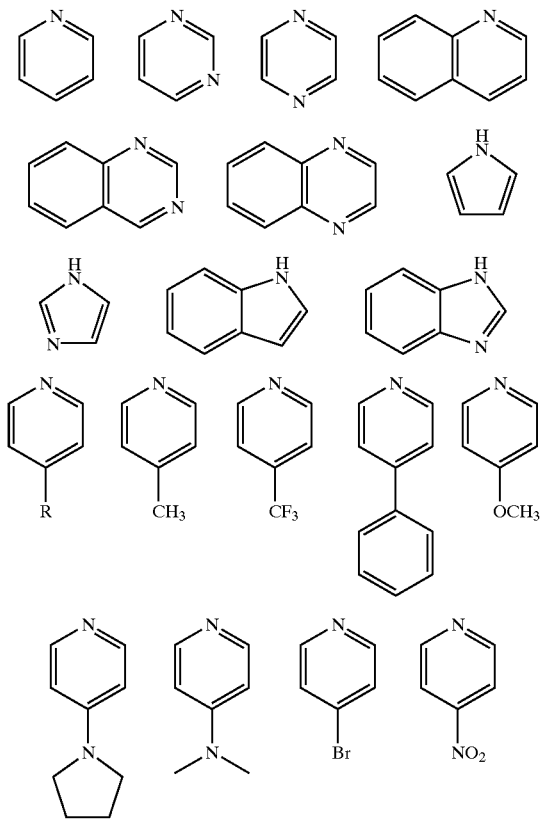

14

-continued

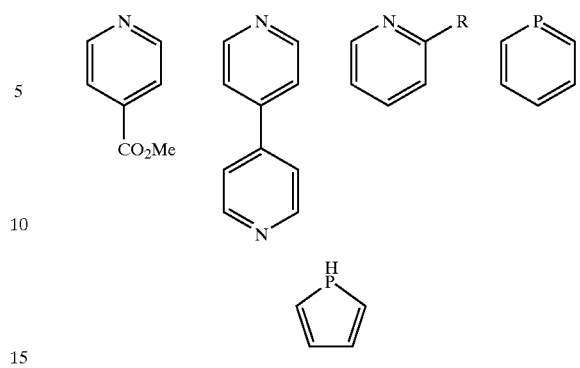

wherein R is selected from the group consisting of hydrogen or a substituent selected from the group consisting of $C_1-C_{20}$ alkyl, $C_2-C_{20}$ alkenyl, $C_2-C_{20}$ alkynyl, aryl, $C_1-C_{20}$ carboxylate, $C_1-C_{20}$ alkoxy, $C_2-C_{20}$ alkenyloxy, $C_2-C_{20}$ alkynyloxy, aryloxy, $C_2-C_{20}$ alkoxycarbonyl, $C_1-C_{20}$ alkylthio, $C_1-C_{20}$ alkylsulfonyl and $C_1-C_{20}$ alkylsulfinyl. Optionally, the R group may be substituted with one or more moieties selected from the group consisting of $C_1-C_{10}$ alkyl, $C_1-C_{10}$ alkoxy, and aryl which in turn may each be further substituted with one or more groups selected from a halogen, a $C_1-C_5$ alkyl, $C_1-C_5$ alkoxy, and phenyl. Moreover, any of the heterocycles may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. Preferably R is selected from the group consisting of $C_1-C_{20}$ alkyl, aryl, ether, amine, halide, nitro, ester and pyridyl.

Preferably complexes 1–4 are used to make the preferred embodiments 5–29 of the inventive complex:

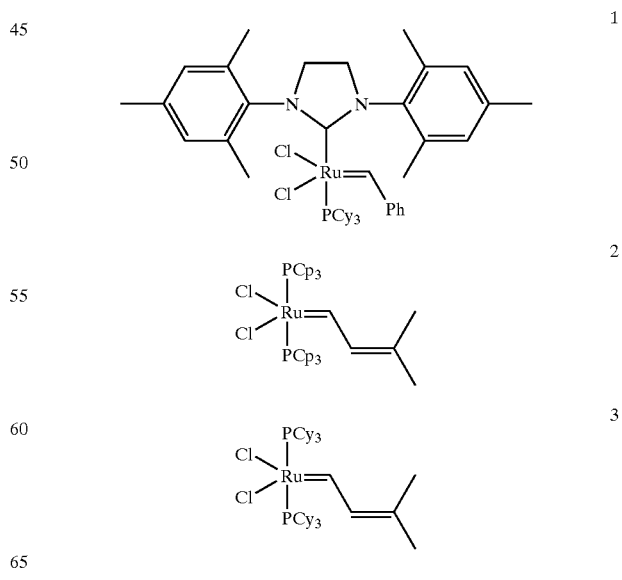

4
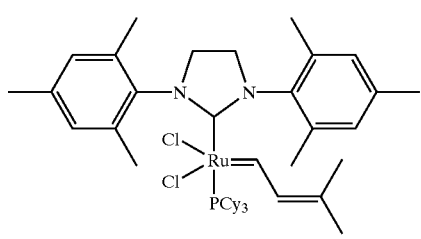
5
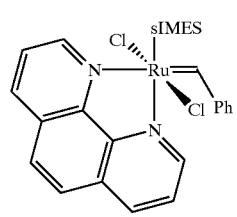
6
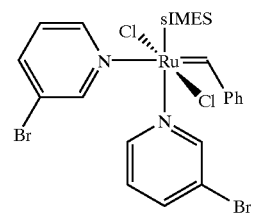
7
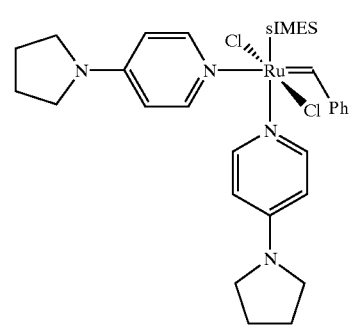
8
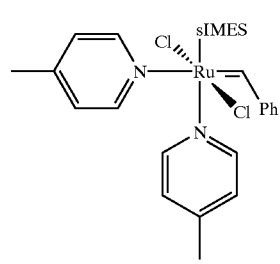
9
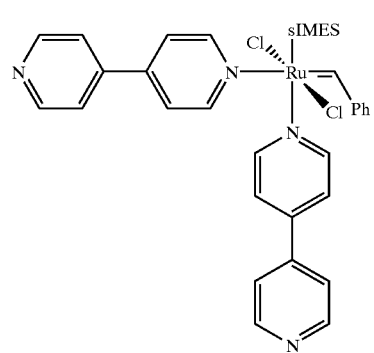
10
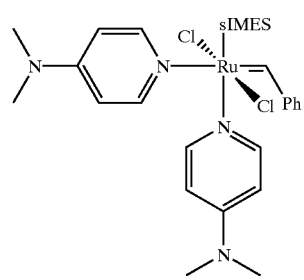
11
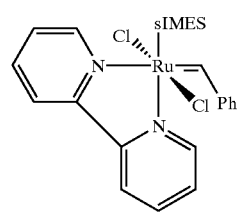
12
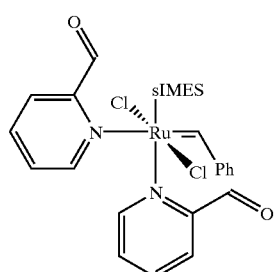
13
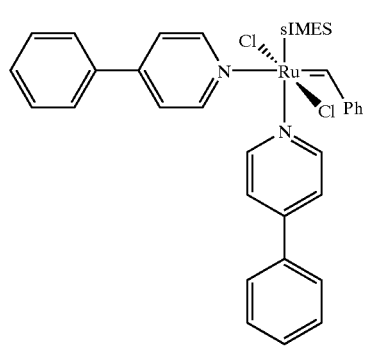
14
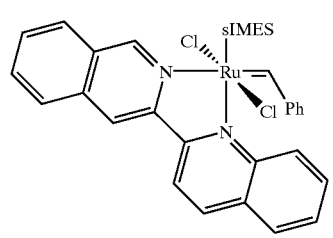
15
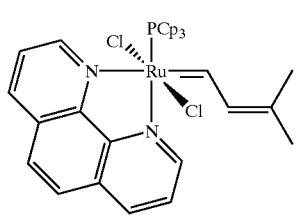

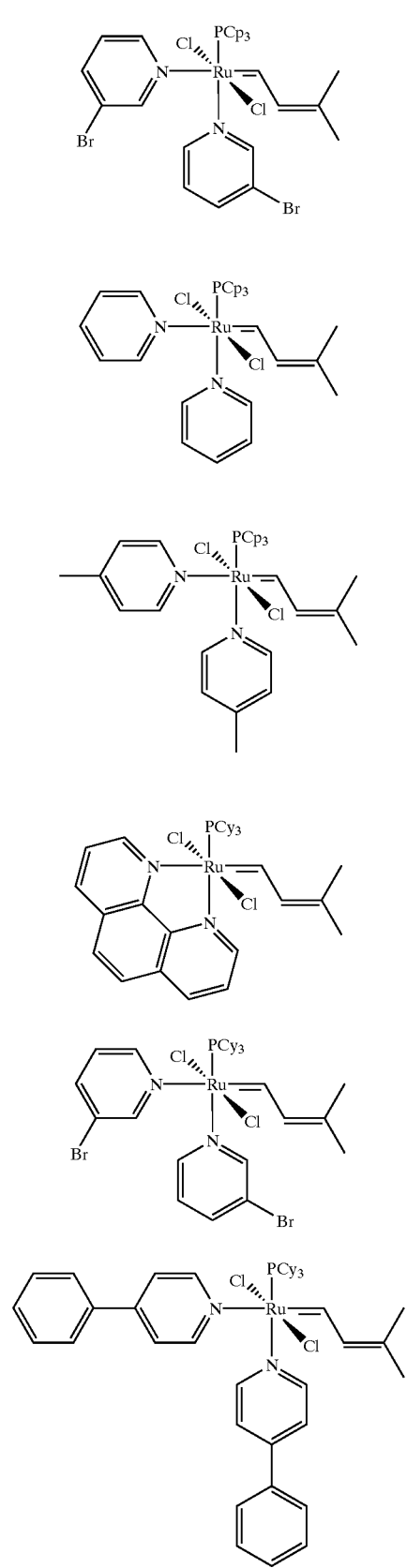
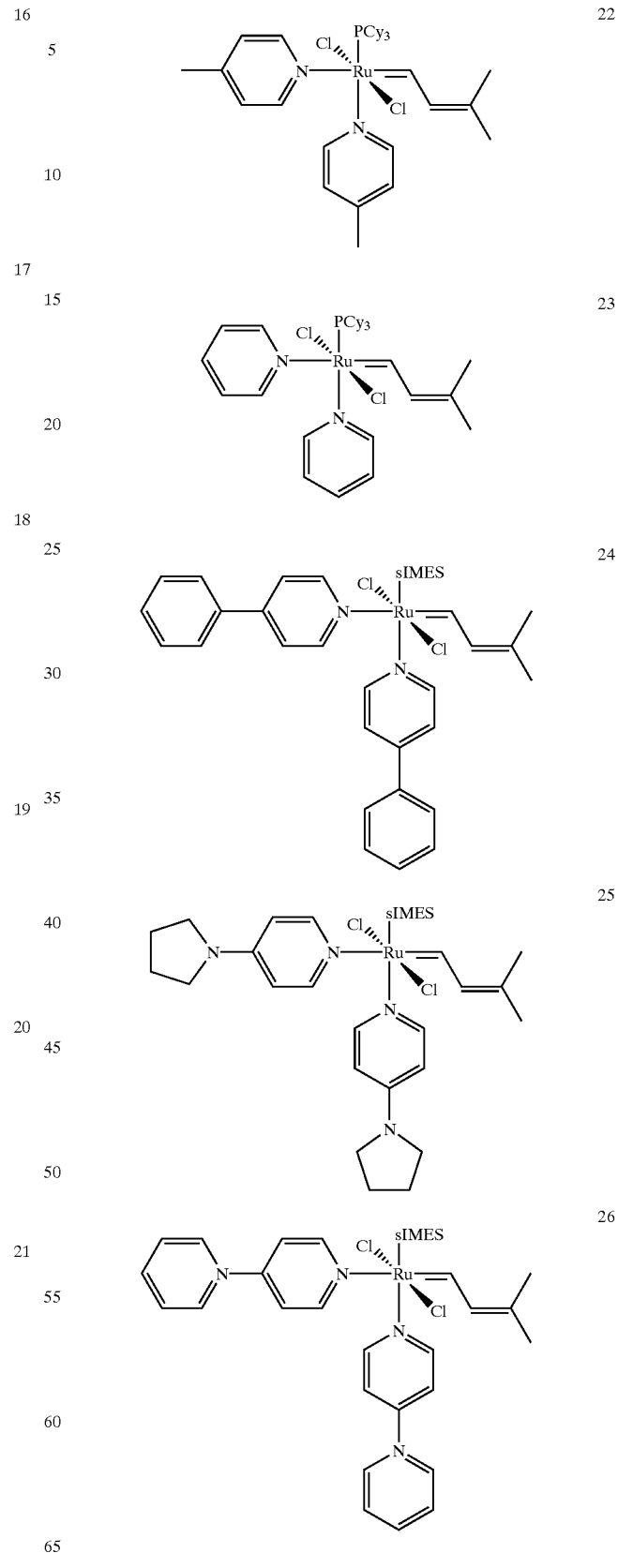

-continued

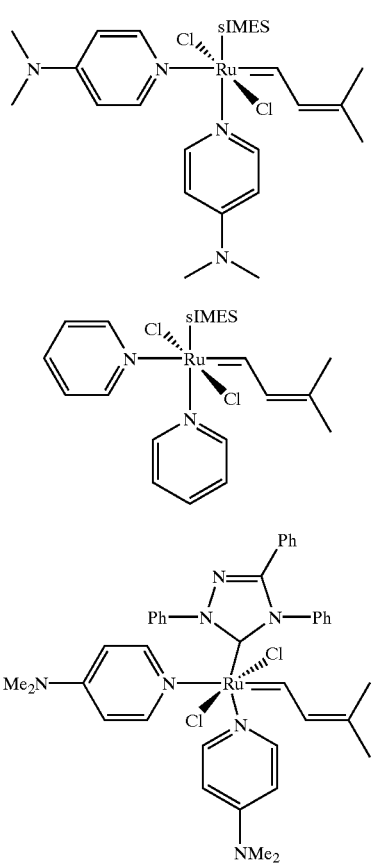

wherein sIMES is

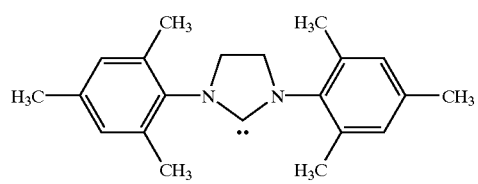

Most preferably, L is an NHC, preferably an imidazolidine ligand, and $L^2$ and $L^{1'}$ are pyridines.

The carbene complexes of the invention may also be cumulated. For example, one aspect of the invention is a catalyst of the general structure:

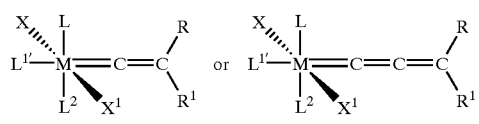

wherein M, L, $L^1$, $L^{1'}$, $L^2$, X, $X^1$, R and $R^1$ are as defined above In all of the above carbene complexes, at least one of L, $L^1$, $L^{1'}$, $L^2$, X, $X^1$, R and $R^1$, may be linked to at least one other of L, $L^1$, $L^{1'}$, $L^2$, X, $X^1$, R and $R^1$ to form a bidentate or multidentate ligand array.

Synthesis

In general, the inventive catalysts are made by contacting excess neutral electron donor ligand, such as a pyridine, with the previously described penta-coordinated metal carbene catalyst complex of the formula:

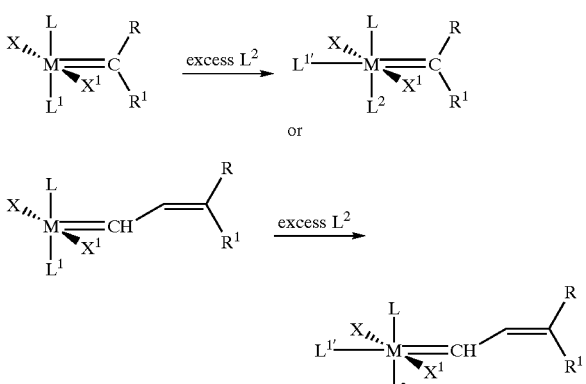

wherein:
M, X, $X^1$, L, $L^1$, R and $R^1$ are as previously defined; and wherein the third neutral electron donor ligand attaches to the metal center. Scheme 1 shows the general synthesis reaction for forming the inventive hexacoordinated metal carbene complexes:

SCHEME 1

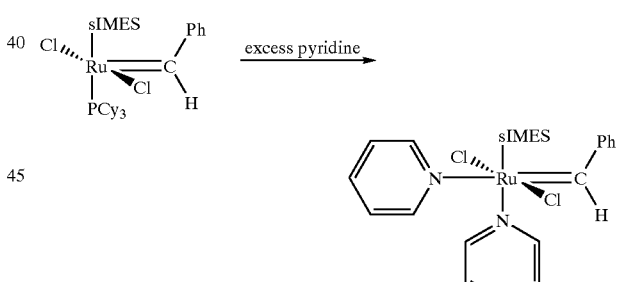

wherein:
M, X, $X^1$, L, $L^1$, $L^{1'}$, $L^2$, R and $R^1$ are as previously defined.

The synthesis of a preferred embodiment is shown in Scheme 2:

SCHEME 2

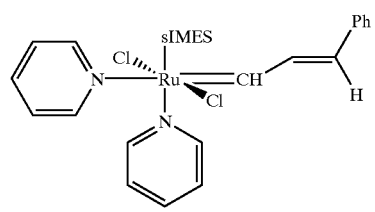

As shown by Schemes 1 and 2, in the presence of excess ligand $L^2$, the pentacoordinated complex loses the $L^1$ ligand and ligands $L^2$ and $L^{1'}$ attach to the metal center. Ligands $L^2$ and $L^{1'}$ may be the same compound, for example, pyridines (when excess pyridine is used), or may together form a bidentate ligand. Alternatively, $L^1$ and $L^{1'}$ may be the same, in which case, the pentacoordinated compound does not necessarily lose the $L^1$ ligand in the presence of excess $L^2$.

The inventive complex may also be a cumulated carbene complex of the general formulas:

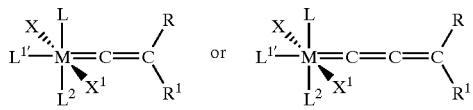

wherein M, X, $X^1$, L, $L^1$, $L^{1'}$, $L^2$, R and $R^1$ are as previously defined. The synthesis of these compounds would follow Scheme 1 except that the starting compound would be a pentacoordinated vinylidene or pentacoordinated cumulene, respectively. The synthesis of preferred embodiments of the vinylidenes can be seen in Scheme 3:

SCHEME 3

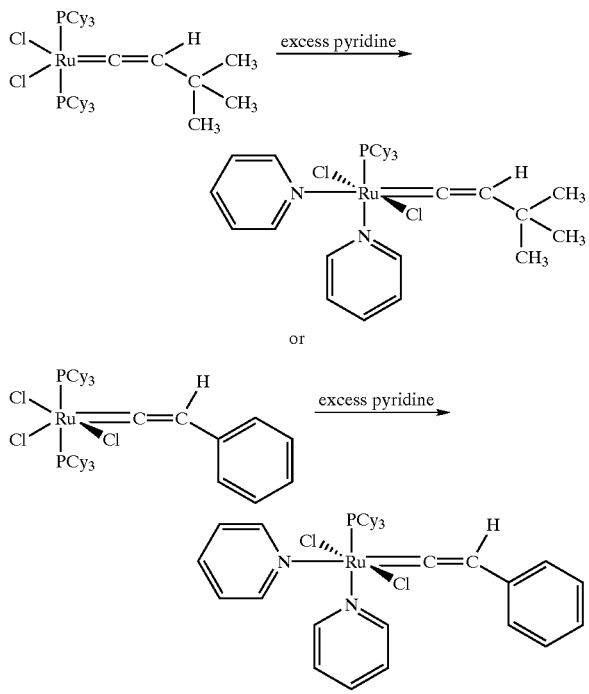

Other preferred compounds synthesized by the inventive method include where $L^2$ and $L^{1'}$ form a bidentate ligand:

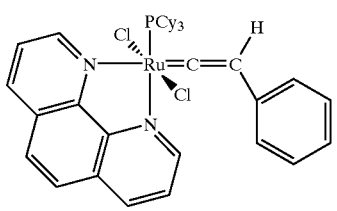

and

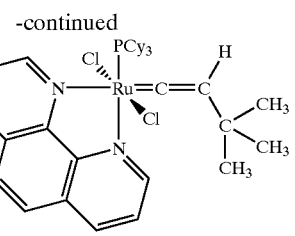

The inventive hexacoordinated catalyst complexes provide synthetic utility and utility in catalytic reactions. Without being bound by theory, these complexes contain substitutionally labile ligands, for example, pyridine and chloride ligands, and serve as a versatile starting material for the synthesis of new ruthenium metal carbene complexes. The chloride ligands are more labile than in the corresponding pentacoordinated phosphine-based complexes. As stated above, X and $X^1$ are any anionic ligand. Preferably X and $X^1$ are selected from the group consisting of chloride, bromide, iodide, Tp, alkoxide, amide, and thiolate. The pyridine ligands are more labile than the phosphines in the corresponding pentacoordinated phosphine-based complexes. Again, as stated above, L, $L^1$, $L^{1'}$, and $L^2$ can be any neutral electron donor ligands, including a NHC ligand. Depending on the size of the ligand, one or two neutral ligands (in addition to the NHC) may bind to the metal center.

Interestingly, the inventive catalyst complexes may be used in both metathesis reactions or the formation of an NHC ligand based complex. As shown in Scheme 4, the hexacoordinated complex can lose a neutral electron donor ligand to produce the pentacoordinated catalyst complex. The reaction may also proceed the other way to produce a hexacoordinated complex in the presence of excess $L^2$.

SCHEME 4

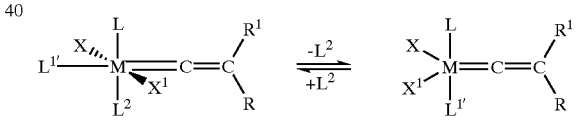

The pentacoordinated complex may also lose the $L^1$ ligand to form the metathesis active tetracoordinated species (Scheme 5):

SCHEME 5

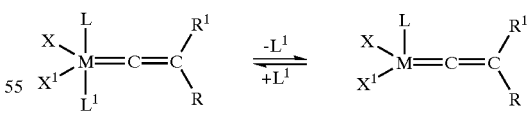

As shown in Scheme 5, the $L^1$ ligand may also attach to a tetracoordinated species to form the pentacoordinated complex.

The tetracoordinated species may then initiate polymerization when in the presence of an olefin, as shown in Scheme 6, or may form the NHC-ligand based pentacoordinated complex when in the presence of a protected NHC-ligand (Scheme 7):

SCHEME 6

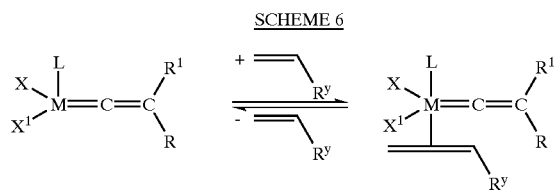

SCHEME 7

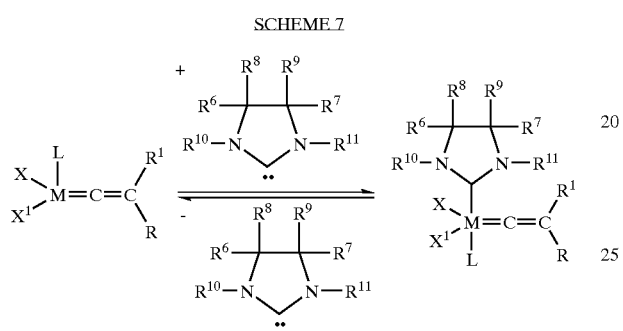

The following structure NHC—A—B indicates generally the protected form of a N-Heterocyclic Carbene (NHC).

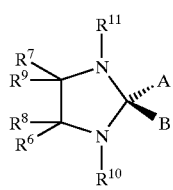

It is also envisioned that the protected NHC—A—B may be of an unsaturated variety, such as

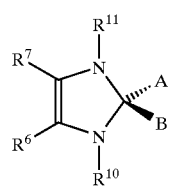

In the above structures, A is preferably H and B may be selected from the group consisting of $CCl_3$; $CH_2SO_2Ph$; $C_6F_5$; $OR^{21}$; and $N(R^{22})(R^{23})$, wherein $R^{21}$ is selected from the group consisting of Me, $C_2H_5$, i-$C_3H_7$, $CH_2CMe_3$, $CMe_3$, $C_6H_{11}$ (cyclohexyl), $CH_2Ph$, $CH_2$norbomyl, $CH_2$norbomenyl, $C_6H_5$, 2,4,6-$(CH_3)_3C_6H_2$ (mesityl), 2,6-i-$Pr_2C_6H_2$, 4-Me—$C_6H_4$ (tolyl), 4-Cl—$C_6H_4$; and wherein $R^{22}$ and $R^{23}$ are independently selected from the group consisting of Me, $C_2H_5$, i-$C_3H_7$, $CH_2CMe_3$, $CMe_3$, $C_6H_{11}$ (cyclohexyl), $CH_2Ph$, $CH_2$norbomyl, $CH_2$norbornenyl, $C_6H_5$, 2,4,6-$(CH_3)_3C_6H_2$ (mesityl), 2,6-i-$Pr_2C_6H_2$, 4-Me-$C_6H_4$ (tolyl), 4-Cl—$C_6H_4$). This approach relates to the thermal generation of a NHC ligand from a stable (protected) NHC derivative with a release of a quantity of A—B. One of the more preferred methods to generate a reactive NHC ligand is to employ a stable carbene precursor where the A—B compound is also a reactive NHC ligand. A detailed description of the protected NHC and related methods of synthesis and use can be seen in U.S. Provisional Patent Application No. 60/278,311 and No. 60/288,680, the contents of each of which are incorporated herein by reference. The following structure for the sImesHCCl₃ shows a preferred embodiment of a protected NHC ligand for use with the inventive hexacoordinated complexes:

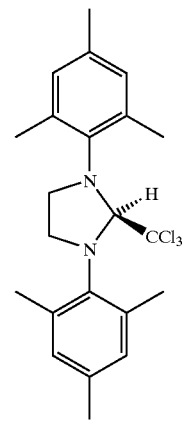

The NHC ligand based pentacoordinated complex may then lose the L ligand to form the metathesis active tetracoordinated species and proceed to initiate the polymerization reaction in the presence of an olefin (Scheme 8):

SCHEME 8

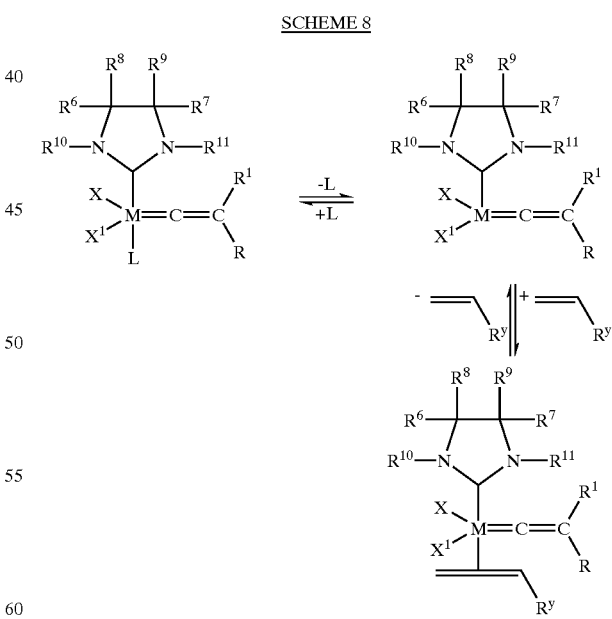

It should also be noted that the hexacoordinated complex can undergo a ligand exchange such that the NHC replaces another neutral electron donor ligand resulting in an NHC ligand based hexacoordinated complex (Scheme 9):

SCHEME 9

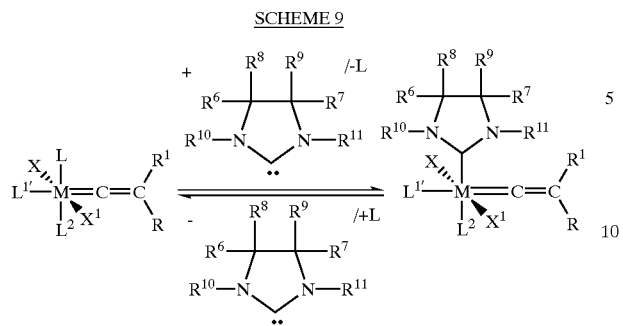

In all the above schemes and complexes M, X, X$^1$, L, L$^1$, L$^{1'}$, L$^2$, R, R$^1$, R$^6$, R$^7$, R$^8$, R$^9$, R$^{10}$, R$^{11}$, and R$^y$ are as previously defined.

The reaction of complex 1 with a large excess (~100 equiv) of pyridine results in a rapid color change from red to bright green, and transfer of the resulting solution to cold (−10° C.) pentane leads to the precipitation of the bis-pyrdine adduct (ImesH$_2$)(Cl)$_2$ (C$_5$H$_5$N)$_2$Ru=CHPh (31). Complex 31 can be purified by several washes with pentane and is isolated as an air-stable green solid that is soluble in CH$_2$Cl$_2$, benzene and THF. This procedure provides complex 31 in 80–85% yield and is easily carried out on a multigram scale.

Crystals suitable for X-ray crystal structure determination were grown by vapor diffusion of pentane into a saturated benzene solution of 31 at room temperature. The collection and refinement parameters for the crystallographic analysis are summarized in Table 1.

TABLE 1

Crystal Data and Structure Refinement for Complex 31

| | |
|---|---|
| Empirical formula | C$_{76}$H$_{84}$Cl$_4$N$_8$Ru$_2$ |
| Formula weight | 1453.46 |
| Crystal habit | Rod |
| Crystal size | 0.41 × 0.11 × 0.07 mm$^3$ |
| Crystal color | Emerald green |
| Diffractometer | CCD area detector |
| Wavelength | 0.71073 Mo Kα |
| Temperature | 98 K |
| Unit Cell Dimensions | a = 12.3873(16) Å |
| | b = 15.529(2) Å |
| | c = 18.562(2) Å |
| | α = 78.475(2)° |
| | β = 81.564(2)° |
| | γ = 76.745(2)° |
| Volume | 3386.2(8) Å$^3$ |
| Z | 4 |
| Crystal system | Triclinic |
| Space group | P1 |
| Density (calculated) | 2.758 Mg/m$^3$ |
| θ range | 1.61–28.51° |
| h min, max | −16, 16 |
| k min, max | −20, 20 |
| l min, max | −24, 24 |
| Reflections collected | 76469 |
| Independent reflections | 15655 |
| GOF on F$^2$ | 1.438 |
| R$_{Int}$ | 0.867 |
| Final R indices [I > 2σ(I)] | 0.0609 |
| Final weighted R (F$_o^2$) | 0.0855 |

A labeled view of complex 31 is shown in FIG. 1 and representative bond lengths and bond angles are reported in Table 2:

TABLE 2

Selected Bond Lengths (Å) and Angles (deg) for Complex 31

| Bond Lengths (Å) | |
|---|---|
| Ru—C(1) | 1.873(4) |
| Ru—N(3) | 2.203(3) |
| Ru—Cl(1) | 2.3995(12) |
| Ru—C(38) | 2.033(4) |
| Ru—N(4) | 2.372(4) |
| Ru—Cl(2) | 2.4227(12) |
| Bond Angles (deg) | |
| C(38)—Ru—C(1) | 93.61(17) |
| C(38)—Ru—N(3) | 176.40(14) |
| C(38)—Ru—N(4) | 102.85(14) |
| C(38)—Ru—Cl(1) | 93.83(12) |
| C(38)—Ru—Cl(2) | 84.39(11) |
| C(1)—Ru—N(3) | 87.07(15) |
| C(1)—Ru—N(4) | 161.18(14) |
| C(1)—Ru—Cl(1) | 100.57(14) |
| C(1)—Ru—Cl(2) | 84.75(14) |
| Cl(1)—Ru—Cl(2) | 174.50(4) |

Several structural isomers of the bis-pyridine adduct can be envisioned, but the solid-state structure reveals that the pyridines bind in a cis geometry, occupying the coordination sites trans to the benzylidene and the N-heterocyclic carbene ligand. The Ru=C(1) (benzylidene carbon) bond length of 1.873(4) Å is slightly longer than those in five-coordinate ruthenium olefin metathesis catalysts, including (Cl)$_2$ (PCy$_3$)$_2$ Ru=CHPh [d(Ru=C$_\alpha$)=1.838(2) Å] and complex 1 [d(Ru=C$_\alpha$)=1.835(2) Å]. The elongated Eu=C$_\alpha$ bond in 31 likely results from the presence of a trans pyridine ligand. The Ru—C(38) (N-heterocyclic carbene) bond length of 2.033(4) Å is approximately 0.05 Å shorter than that in complex 1, which is likely due to the relatively small size and moderate trans influence of pyridine relative to PCy$_3$. The 0.15 Å difference in the Ru—C(1) and Ru—C(38) bond distances highlights the covalent nature of the former and the dative nature of the latter ruthenium-carbene bond. Interestingly, the two Ru—N bond distances differ by more than 0.15 Å, indicating that the benzylidene ligand exerts a significantly larger trans influence than the N-heterocyclic carbene.

Figure 2:
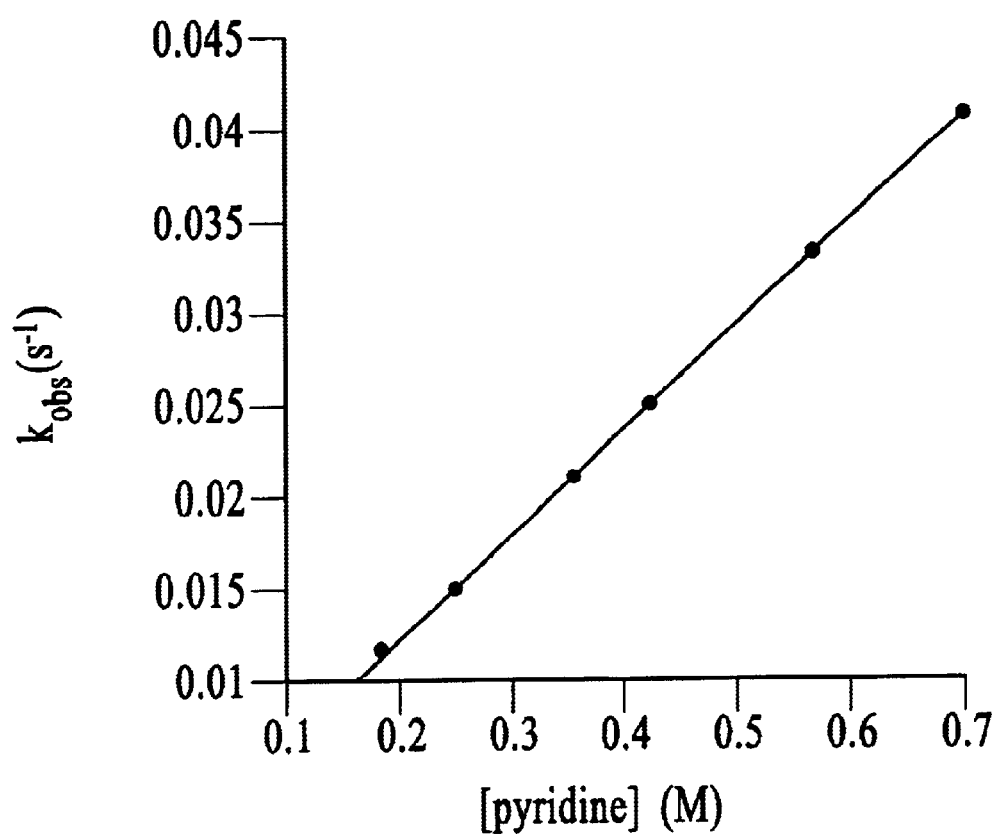

The kinetics of the reaction between complex 1 and pyridine was investigated in order to determine the mechanism of this ligand substitution. The reaction of complex 1 (0.88 M in toluene) with an excess of pyridine-d$_5$ (0.18–0.69 M) is accompanied by a 150 nm red shift visible MLCT absorbance, and this transformation can be followed by UV-vis spectroscopy. The disappearance of starting material (502 nm) was monitored at 20° C., and in all cases, the data fit first-order kinetics over five half-lives. A plot of k$_{obs}$ versus [C5D5N] is presented in FIG. 2. The data show an excellent linear fit (R$^2$=0.999) even at high concentrations of pyridine, and the y-intercept of this line (1.1×10$^{-3}$) is very close to zero. The rate constant for phosphine dissociation (k$_B$) in complex 1 has been determined independently by $^{31}$p magnetization transfer experiments, and at 20° C., k$_B$ is 4.1×10$^{-5}$ s$^{-1}$. This value of k$_B$ places an upper limit on the rate of dissociative ligand exchange in 1, and the observed rate constants for pyridine substitution are clearly 3 orders of magnitude larger than k$_B$. Taken together, these results indicate that the substitution of PCy$_3$ with pyridine proceeds by an associative mechanism with a second-order rate constant of 5.7×10$^{-2}$M$^{-1}$s$^{-1}$ at 20° C. In marked contrast, displacement of the phosphine ligand of 1 with olefinic substrates (which is the initiation event in olefin metathesis reactions) occurs via a dissociative mechanism.

Initial reactivity studies of complex 31 revealed that both pyridine ligands are substitutionally labile. For example, benzylidene 31 reacts instantaneously with 1.1 equiv. of $PCy_3$ to release pyridine and regenerate complex 1. This equilibrium can be driven back toward the pyridine adduct by addition of an excess of $C_5D_5N$, but it is readily reestablished by removal of the volatiles under vacuum.

The facile reaction of 31 with $PCy_3$ suggested that the pyridines may be displaced by other incoming ligands and it was discovered that reaction of the bis-pyridine complex with a wide variety of phosphines provides a simple and divergent route to new ruthenium benzylidenes of the general formula $(ImesH_2)(PR_3)(Cl)_2Ru=CHPh$. The combination of 31 and 1.1 equiv. of $PR_3$ results in a color change from green to red/brown and formation of the corresponding $PR_3$ adduct. The residual pyridine can be removed under vacuum, and the ruthenium products are purified by several washes with pentane and/or by column chromatography. This ligand substitution works well for a variety of alkyl- and aryl-substituted phosphines including $PPH_3$, $PBn_3$, and $P(n-Bu)_3$ to produce complexes 32, 33 and 34.

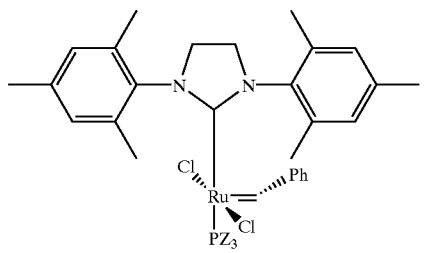

Z = Ph (32)
Z = Bn (33)
Z = (n-Bu) (34)
Z = (p-CF$_3$C$_6$H$_4$) (35)
Z = (p-ClC$_6$H$_4$) (36)
Z = (p-MeOC$_6$H$_4$) (37)

Additionally, the para-substituted triphenylphosphine derivatives 35, 36 and 37 (containing para substituents $CF_3$, Cl, and OMe, respectively) can be prepared using the inventive method. The synthetic accessibility of complex 35 is particularly remarkable, because $P(p-CF_3C_6H_4)_3$ is an extremely electron-poor phosphine ($\chi=20.5$ cm$^{-1}$) The triarylphosphine ruthenium complexes 32, 35–37 are valuable catalysts as they are almost 2 orders of magnitude more active for olefin metathesis reactions than the parent complex 1.

There appear to be both steric and electronic limitations on the incoming phosphine ligand in the pyridine substitution reaction. For example, complex 31 does not react with $P(o-tolyl)_3$ to produce a stable product, presumably due to the prohibitive size of the incoming ligand. The cone angle of $P(o-tolyl)_3$ is 194°, while that of $PCy_3$ (one of the larger phosphines shown to successfully displace the pyridines of 31) is 170°. Additionally, the electron-poor phosphine $P(C_6F_6)_3$ shows no reaction with 31, even under forcing conditions. This ligand has a significantly lower electron donor capacity ($\chi=33.6$ cm$^{-1}$) than $P(p-CF_3C_6H_4)_3$ ($\chi=20.5$ cm$^{-1}$) and also has a larger cone angle than $PCy_3$ ($\theta=184°$).

The methodology described herein represents a dramatic improvement over previous synthetic routes to the complexes $(NHC)(PR_3)(Cl)_2Ru=CHPh$. Earlier preparations of these compounds involved reaction of the bis-phosphine precursor $(PR_3)_2(Cl)_2Ru=CHPh$ with an NHC ligand. These transformations were often low yielding (particularly when the NHC was small), and required the parallel synthesis of ruthenium precursors containing each $PR_3$ ligand. Furthermore, bis-phosphine starting materials containing $PR_3$ ligands that are smaller and less electron-donating than $PPh_3$ ($\theta=145°$; $\chi=13.25$ cm$^{-1}$; $pK_a=2.73$) cannot be prepared, placing severe limitations on the complexes that are available by the earlier preparation methods.

The chlorine ligands of 31 are also substantially labile relative to those in the parent complex 1. For example, 31 reacts quantitatively with NaI within 2 hours at room temperature to afford $(ImesH_2)(I)_2 (C_5H_5N)Ru=CHPh$ (38). In contrast, the reaction between 1 and NaI takes approximately 8 hours to reach completion under identical conditions. Interestingly, $^1H$ NMR spectroscopy reveals that the diiodide complex 38 contains only one pyridine ligand, while the analogous dichloride species 31 coordinates 2 equiv. of pyridine. The relatively large size of the iodide ligands and the lower electrophilicity at the metal center in 38 (as compared to 31) are both believed to contribute to the formation of a five-coordinate complex in this system.

Complex 31 also reacts quantitatively with KTp [Tp=tris(pyrazolyl)borate] within 1 h at 25° C. to produce the bright green product $Tp(ImesH_2)(Cl)Ru=CHPh$ (39), while the analogous reaction between complex 1 and KTp is extremely slow. (The latter proceeds to less than 50% completion even after several days at room temperature). Removal of the solvents under vacuum followed by filtration and several washes with pentane and methanol provides 39 as an air and moisture stable solid. Preliminary $^1H$ NMR studies also show that the combination of 31 with an excess of KO$^t$-Bu produces the four-coordinate benzylidene, $(ImesH_2)-(O^tBu)_2Ru=CHPh$ (40), quantitatively within 10 min. at ambient temperature. In contrast, the reaction between 1 and KO$^t$-Bu to form 40 does not proceed to completion, even after several days at 35° C. Complex 40 may be considered a model for the 14-electron intermediate, $(IMesH_2)(Cl)_2Ru=CHPh$, involved in olefin metathesis reactions of 1.

The invention provides a high-yielding procedure for the preparation of $(IMesH_2)(Cl)_2 (C_5H_5N)_2Ru=CHPh$ (31) from $(IMesH_2)(Cl)_2 (PCy_3)Ru=CHPh$ (1). In contrast to the reaction of 1 with olefinic substrates, this ligand substitution proceeds by an associative mechanism. Complex 31 reacts readily with phosphines, providing access to new complexes discussed herein. Complex 31 also undergoes reaction with KO$^t$-Bu, NaI, and KTp to provide new four-, five-, and six-coordinate ruthenium benzylidenes. The inventive methodology is useful for facilitating the development of new ruthenium olefin metathesis catalysts containing structurally diverse ligand arrays.

Olefin Metathesis

The inventive complexes are useful in olefin metathesis reactions, particularly for polymerization reactions. These catalysts can be used in various metathesis reactions, including but not limited to, ring-opening metathesis polymerization of strained and unstrained cyclic olefins, ring-closing metathesis of acyclic dienes, acyclic diene metathesis polymerization ("ADMET"), self- and cross-metathesis reactions, alkyne polymerization, carbonyl olefination, depolymerization of unsaturated polymers, synthesis of telechelic polymers, and olefin synthesis.

The most preferred olefin monomer for use in the invention is substituted or unsubstituted dicyclopentadiene (DCPD). Various DCPD suppliers and purities may be used such as Lyondell 108 (94.6% purity), Veliscol UHP (99+% purity), B.F. Goodrich Ultrene® (97% and 99% purities), and Hitachi (99+% purity). Other preferred olefin monomers include other cyclopentadiene oligomers including trimers, tetramers, pentamers, and the like; cyclooctadiene (COD;

DuPont); cyclooctene (COE, Alfa Aesar); cyclohexenylnorbornene (Shell); norbornene (Aldrich); norbornene dicarboxylic anhydride (nadic anhydride); norbornadiene (Elf Atochem); and substituted norbornenes including butyl norbornene, hexyl norbornene, octyl norbornene, decyl norbornene, and the like. Preferably, the olefinic moieties include mono-or disubstituted olefins and cycloolefins containing between 3 and 200 carbons. Most preferably, metathesis-active olefinic moieties include substituted or unsubstituted cyclic or multicyclic olefins, for example, cyclopropenes, cyclobutenes, cycloheptenes, cyclooctenes, [2.2.1]bicycloheptenes, [2.2.2]bicyclooctenes, benzocyclobutenes, cyclopentenes, cyclopentadiene oligomers including trimers, tetramers, pentamers, and the like; cyclohexenes. It is also understood that such compositions include frameworks in which one or more of the carbon atoms carry substituents derived from radical fragments including halogens, pseudohalogens, alkyl, aryl, acyl, carboxyl, alkoxy, alkyl- and arylthiolate, amino, aminoalkyl, and the like, or in which one or more carbon atoms have been replaced by, for example, silicon, oxygen, sulfur, nitrogen, phosphorus, antimony, or boron. For example, the olefin may be substituted with one or more groups such as thiol, thioether, ketone, aldehyde, ester, ether, amine, amide, nitro, carboxylic acid, disulfide, carbonate, isocyanate, phosphate, phosphite, sulfate, sulfite, sulfonyl, carbodiimide, carboalkoxy, carbamate, halogen, or pseudohalogen. Similarly, the olefin may be substituted with one or more groups such as $C_1$–$C_{20}$ alkyl, aryl, acyl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, arylthio, $C_1$–$C_{20}$ alkylsulfonyl, and $C_1$–$C_{20}$ alkylsulfinyl, $C_1$–$C_{20}$ alkylphosphate, arylphosphate, wherein the moiety may be substituted or unsubstituted.

These olefin monomers may be used alone or mixed with each other in various combinations to adjust the properties of the olefin monomer composition. For example, mixtures of cyclopentadiene dimer and trimers offer a reduced melting point and yield cured olefin copolymers with increased mechanical strength and stiffness relative to pure poly-DCPD. As another example, incorporation of COD, norbornene, or alkyl norbornene co-monomers tend to yield cured olefin copolymers that are relatively soft and rubbery. The resulting polyolefin compositions formed from the metathesis reactions are amenable to thermosetting and are tolerant of additives, stabilizers, rate modifiers, hardness and/or toughness modifiers, fillers and fibers including, but not limited to, carbon, glass, aramid (e.g., Kevlar® and Twaron®), polyethylene (e.g., Spectra® and Dyneema®), polyparaphenylene benzobisoxazole (e.g., Zylon®), polybenzamidazole (PBI), and hybrids thereof as well as other polymer fibers.

The metathesis reactions may optionally include formulation auxiliaries. Known auxiliaries include antistatics, antioxidants (primary antioxidants, secondary antioxidants, or mixtures thereof), ceramics, light stabilizers, plasticizers, dyes, pigments, fillers, reinforcing fibers, lubricants, adhesion promoters, viscosity-increasing agents, and demolding enhancers. Illustrative examples of fillers for improving the optical physical, mechanical, and electrical properties include glass and quartz in the form of powders, beads, and fibers, metal and semi-metal oxides, carbonates (e.g. $MgCO_3$, $CaCO_3$), dolomite, metal sulfates (e.g. gypsum and barite), natural and synthetic silicates (e.g. zeolites, wollastonite, and feldspars), carbon fibers, and plastics fibers or powders.

The UV and oxidative resistance of the polyolefin compositions resulting from the metathesis reactions using the inventive carbene complex may be enhanced by the addition of various stabilizing additives such as primary antioxidants (e.g., sterically hindered phenols and the like), secondary antioxidants (e.g., organophosphites, thioesters, and the like), light stabilizers (e.g., hindered amine light stabilizers or HALS), and UV light absorbers (e.g., hydroxy benzophenone absorbers, hydroxyphenylbenzotriazole absorbers, and the like), as described in U.S. application Ser. No. 09/498, 120, filed Feb. 4, 2000, the contents of which are incorporated herein by reference.

Exemplary primary antioxidants include, for example, 4,4'-methylenebis (2,6-di-tertiary-butylphenol) (Ethanox 702®; Albemarle Corporation), 1,3,5-trimethyl-2,4,6-tris (3,5-di-tert-butyl-4-hydroxybenzyl) benzene (Ethanox 330®; Albermarle Corporation), octadecyl-3-(3',5'-di-tert-butyl-4'-hydroxyphenyl) propionate (Irganox 1076®; Ciba-Geigy), and pentaerythritol tetrakis(3-(3,5-di-tert-butyl-4-hydroxyphenyl)propionate)(Irganox® 1010; Ciba-Geigy). Exemplary secondary antioxidants include tris(2,4-ditert-butylphenyl)phosphite (Irgafos® 168; Ciba-Geigy), 1:11(3, 6,9-trioxaudecyl)bis(dodecylthio)propionate (Wingstay® SN-1; Goodyear), and the like. Exemplary light stabilizers and absorbers include bis(1,2,2,6,6-pentamethyl-4-piperidinyl)-[[3,5-bis(1,1-dimethylethyl)-4-hydroxyphenyl] methyl]butylmalonate (Tinuvin® 144 HALS; Ciba-Geigy), 2-(2H-benzotriazol-2-yl)-4,6-ditertpentylphenol (Tinuvino® 328 absorber; Ciba-Geigy), 2,4-di-tert-butyl-6-(5-chlorobenzotriazol-2-yl)phenyl (Tinuvin® 327 absorber; Ciba-Geigy), 2-hydroxy-4-(octyloxy)benzophenone (Chimassorb® 81 absorber; Ciba-Geigy), and the like.

In addition, a suitable rate modifier such as, for example, triphenylphosphine (TPP), tricyclopentylphosphine, tricyclohexylphosphine, triisopropylphosphine, trialkylphosphites, triarylphosphites, mixed phosphites, or other Lewis base, as described in U.S. Pat. No. 5,939,504 and U.S. application Ser. No. 09/130,586, the contents of each of which are herein incorporated by reference, may be added to the olefin monomer to retard or accelerate the rate of polymerization as required.

The resulting polyolefin compositions, and parts or articles of manufacture prepared therefrom, may be processed in a variety of ways including, for example, Reaction Injection Molding (RIM), Resin Transfer Molding (RTM) and vacuum-assisted variants such as VARTM (Vacuum-Assisted RTM) and SCRIMP (Seemann Composite Resin Infusion Molding Process), open casting, rotational molding, centrifugal casting, filament winding, and mechanical machining. These processing compositions are well known in the art. Various molding and processing techniques are described, for example, in PCT Publication WO 97/20865, the disclosure of which is incorporated herein by reference.

The metathesis reactions may occur in the presence or absence of a solvent. Examples of solvents that can be used in the polymerization reaction include organic, protic, or aqueous solvents, which are preferably inert under the polymerization conditions. Examples of such solvents include aromatic hydrocarbons, chlorinated hydrocarbons, ethers, aliphatic hydrocarbons, alcohols, water, or mixtures thereof. Preferred solvents include benzene, toluene, p-xylene, methylene chloride, dichloroethane, dichlorobenzene, chlorobenzene, tetrahydrofuran, diethylether, pentane, methanol, ethanol, water or mixtures thereof. More preferably, the solvent is benzene, toluene, p-xylene, methylene chloride, dichloroethane, dichlorobenzene, chlorobenzene, tetrahydrofuran, diethylether, pentane, methanol, ethanol, or mixtures thereof. Most preferably, the solvent is toluene, or a mixture of benzene and methylene chloride. The solubility of the polymer formed in the polymerization reaction will depend on the choice of solvent and the molecular weight of the polymer obtained.

The inventive complexes have a well-defined ligand environment that enables flexibility in modifying and fine-tuning the activity level, stability, solubility and ease of recovery of these catalysts. The solubility of the carbene compounds may be controlled by proper selection of either hydrophobic or hydrophilic ligands as is well known in the art. The desired solubility of the catalyst will largely be determined by the solubility of the reaction substrates and reaction products.

The inventive metal carbene complexes have shown a high rate of initiation allowing for most, if not all, of the complex added to the reaction to be consumed. Thus, less catalyst is wasted in the metathesis reaction. In contrast, the previous pentacoordinated initiators had a higher amount of extractibles (i.e. unpolymerized monomer) remaining after the reaction concluded. The rate of propagation is also slowed by the presence of the two pyridine ligands. The high rate of initiation and low rate of propagation yields polymers with narrow polydisperities relative to those achieved with the earlier pentacoordinated complexes. Moreover, it was determined that heat increases the rate of the initiation. Thermal initiation of the pentacoordinated complexes can be seen in U.S. Pat. No. 6,107,420, the contents of which are incorporated herein by reference. In general, the initiation and/or rate of the metathesis polymerization using the inventive catalysts is controlled by a method comprising contacting the inventive catalyst with an olefin and heating the reaction mixture. In a surprising and unexpected result, the $T_{max}$ for the thermal initiation of the inventive catalyst is significantly higher than the $T_{max}$ for the previous pentacoordinated catalysts. Without being bound by theory, this is significant in that in a reaction using a metathesis catalyst, if the part or article being prepared is a type of filled system (e.g., a system containing reinforcing fillers, fibers, beads, etc.), the filling material may act as a heat sink. With the previous pentacoordinated catalysts, post-curing was sometimes necessary due to the effect of the heat sink resulting from a filled system. ROMP polymerization in the presence of peroxide cross linking agents using pentacoordinated catalysts is discussed in U.S. Pat. No. 5,728,785, the contents of which are incorporated herein by reference. In contrast, the reactions using the inventive hexacoordinated catalysts generate significantly more internal heat. This high $T_{max}$ reduces the need for post cure. Additionally, even if peroxides or radicals are added to promote crosslinking, the degree of crosslinking in the part that uses the radical mechanism is increased in comparison to a part prepared using the previous pentacoordinated metathesis catalysts. Moreover, the half-life is dependent on the maximum temperature. Using the inventive catalysts, the half life is reduced substantially, and therefore less catalyst is needed, providing a significant commercial advantage. Without being bound by theory, the higher $T_{max}$ indicates that in a ROMP reaction, more rings are opened, and there is a better degree of cure. With a higher $T_{max}$, the extractibles are almost to zero, indicating that almost every molecule that can be reacted is reacted. For example, the vinylidenes are advantageous in that they are more stable at higher temperatures than the alkylidenes. When the protected NHC (e.g., a saturated Imes ligand as described in U.S. Provisional Patent Application No. 60/288,680 and No. 60/278,311, the contents of each of which are incorporated herein by reference), is added to the reaction mixture, a dramatic increase in peak exotherm is seen. Additionally, the time to reach the peak is significantly reduced. A high peak exotherm means more catalyst is available for polymerization, indicating that the extractibles are close to zero. Accordingly, the inventive catalysts have better conversion, better properties, even in the presence of fillers and additives.

For the purposes of clarity, the specific details of the invention will be illustrated with reference to especially preferred embodiments. However, it should be appreciated that these embodiments and examples are for the purposes of illustration only and are not intended to limit the scope of the invention.

EXAMPLES

General Procedures

Manipulation of organometallic compounds was performed using standard Schlenk techniques under an atmosphere of dry argon or in a nitrogen-filled Vacuum Atmospheres drybox ($O_2$<2 ppm). NMR spectra were recorded on a Varian Inova (499.85 MHz for $^1$H; 202.34 MHz for $^{31}$P; 125.69 MHz for $^{13}$C) or a Varian Mercury 300 (299.817 for $^1$H; 121.39 MHz for $^{31}$P; 74.45 MHz for $^{13}$C). $^{31}$P NMR spectra were referenced using $H_3PO_4$ ($\delta$=0 ppm) as an external standard. UV-vis spectra were recorded on an HP 8452A diode-array spectrophotometer.

Materials and Methods

Pentane, toluene, benzene, and benzene-$d_6$ were dried by passage through solvent purification columns. Pyridine was dried by vacuum transfer from $CaH_2$. All phosphines as well as KTp were obtained from commercial sources and used as received. Ruthenium complex 1 was prepared according to literature procedures.

Synthesis of ($IMesH_2$)($C_{12}H_8N_2$)($Cl)_2$Ru=CHPh

Complex 1 (2.0 grams) was dissolved in toluene (10 mL), and 1,10-phenanthroline (0.85 grams, 2 mol equivalents) was added. The reaction flask was purged with argon and the reaction mixture was stirred for approximately 12 hours at about 20° C. to about 25° C. during which time a color change from dark purple to brown-orange was observed. The reaction mixture was transferred into 75 mL of cold (about 0° C.) pentane, and a brown-orange solid precipitated. The precipitate was filtered, washed with 4×20 mL of cold pentane, and dried under vacuum to afford ($IMesH_2$)($C_{12}H_8N_2$)($Cl)_2$Ru=CHPh 5 as an brown-orange powder (1.7 gram, 96% yield).

Synthesis of ($IMesH_2$)($C_5H_4BrN)_2$($Cl)_2$Ru=CHPh

Complex 1 (2.0 grams) was dissolved in toluene (10 mL), and 3-bromopyridine (1.50 grams, 4 mol equivalents) was added. The reaction flask was purged with argon and the reaction mixture was stirred for approximately 12 hours at about 20° C. to about 25° C. during which time a color change from dark purple to light green was observed. The reaction mixture was transferred into 75 mL of cold (about 0° C.) pentane, and a light green solid precipitated. The precipitate was filtered, washed with 4×20 mL of cold pentane, and dried under vacuum to afford ($IMesH_2$)($C_5H_4BrN)_2$($Cl)_2$Ru=CHPh 6 as a light green powder (1.8 grams, 86% yield).

Synthesis of ($IMesH_2$)($C_9H_{12}N_2)_2$($Cl)_2$Ru=CHPh

Complex 1 (2.0 grams) was dissolved in toluene (10 mL), and 4-pyrrolidinopyridine (1.40 grams, 4 mol equivalents) was added. The reaction flask was purged with argon and the reaction mixture was stirred for approximately 12 hours at about 20° C. to about 25° C. during which time a color change from dark purple to light green was observed. The reaction mixture was transferred into 75 mL of cold (about 0° C.) pentane, and a light green solid precipitated. The precipitate was filtered, washed with 4×20 mL of cold pentane, and dried under vacuum to afford (IMesH$_2$) (C$_9$H$_{12}$N$_2$)$_2$(Cl)$_2$Ru=CHPh 7 as a light green powder (1.9 gram, 93% yield).

$^1$H NMR (300 MHz, CD$_2$Cl$_2$): δ19.05 (s, 1H, CHPh), 8.31 (d, 2H, pyridine CH, J$_{HH}$=6.6 Hz), 7.63 (d, 2H, ortho CH, J$_{HH}$=8.4 Hz), 7.49 (t, 1H, para CH, J$_{HH}$=7.4 Hz), 7.33 (d, 2H, pyridine CH, J$_{HH}$=6.9 Hz), 7.10 (t, 2H, meta CH, J$_{HH}$=8.0 Hz), 7.03 (br. s, 2H, Mes CH), 6.78 (br. s, 2H, Mes CH), 6.36 (d, 2H, pyridine CH, J$_{HH}$=6.3 Hz), 6.05 (d, 2H, pyridine CH, J$_{HH}$=6.9 Hz), 4.08 (br. d, 4H, NCH$_2$CH$_2$N), 3.30 (m, 4H, pyrrolidine CH$_2$), 3.19 (m, 4H, pyrrolidine CH$_2$), 2.61–2.22 (multiple peaks, 18H, Mes CH$_3$), 2.02 (m, 4H, pyrrolidine CH$_2$), 1.94 (m, 4H, pyrrolidine CH$_2$).

EXAMPLE

A 75 gram mass of DCPD (containing about 24% trimerized DCPD) was polymerized using (IMesH$_2$)(C$_9$H$_{12}$N$_2$)$_2$(Cl)$_2$Ru=CHPh=0.0151 grams at a DCPD:Ru ratio of (about 30,000:1) at a starting temperature of about 24.2° C. Result: Time to reach maximum temperature (T$_{max}$)=194 seconds. T$_{max}$=208.9° C. Glass transition temperature measured by thermal mechanical analysis (TMA)=165° C. Percent residual monomer (toluene extraction at room temperature)=1.23%.

Synthesis of (IMesH$_2$)(C$_6$H$_7$N)$_2$(Cl)$_2$Ru=CHPh

Complex 1 (2.0 grams) was dissolved in toluene (10 mL), and 4-methylpyridine (0.88 grams, 4 mol equivalents) was added. The reaction flask was purged with argon and the reaction mixture was stirred for approximately 12 hours at about 20° C. to about 25° C. during which time a color change from dark purple to light green was observed. The reaction mixture was transferred into 75 mL of cold (about 0° C.) pentane, and a light green solid precipitated. The precipitate was filtered, washed with 4×20 mL of cold pentane, and dried under vacuum to afford (IMesH$_2$) (C$_6$H$_7$N)$_2$(Cl)$_2$Ru=CHPh 8 as an light green powder (1.5 grams, 84% yield).

Synthesis of (IMesH$_2$)(C$_{10}$H$_8$N$_2$)$_2$(Cl)$_2$Ru=CHPh

Complex 1 (2.0 grams) was dissolved in toluene (10 mL), and 4,4'-bipyridine (0.74 grams, 2 mol equivalents) was added. The reaction flask was purged with argon and the reaction mixture was stirred for approximately 12 hours at about 20° C. to about 25° C. during which time a color change from dark purple to brown-orange was observed. The reaction mixture was transferred into 75 mL of cold (about 0° C.) pentane, and an brown-orange solid precipitated. The precipitate was filtered, washed with 4×20 mL of cold pentane, and dried under vacuum to afford (IMesH$_2$) (C$_{10}$H$_8$N$_2$)$_2$(Cl)$_2$Ru=CHPh 9 as a brown-orange powder (1.4 gram, 71% yield).

$^1$H NMR (500 MHz, CD$_2$Cl$_2$): δ19.15 (s, 1H, CHPh), 8.73–8.68 (multiple peaks, 8H pyridine CH), 7.63–6.77 (multiple peaks, 17H, pyridine CH, para CH, meta CH, Mes CH), 4.08 (br. d, 4H, NCH$_2$CH$_2$N), 2.61–2.24 (multiple peaks, 18H, Mes CH$_3$).

Polymerization Example

A 75 gram mass of DCPD (containing about 24% trimerized DCPD) was polymerized using (IMesH$_2$)(C$_{10}$H$_8$N$_2$)$_2$(Cl)$_2$Ru=CHPh=0.0153 grams at a DCPD:Ru ratio of (about 30,000:1) at a starting temperature of about 24.2° C. Result: Time to reach maximum temperature (T$_{max}$)=953 seconds. T$_{max}$=124.2° C.

Synthesis of (IMesH$_2$)(C$_7$H$_{10}$N$_2$)$_2$(Cl)$_2$Ru=CHPh

Complex 1 (2.0 grams) was dissolved in toluene (10 mL), and 4-dimethylaminopyridine (1.18 grams, 4 mol equivalents) was added. The reaction flask was purged with argon and the reaction mixture was stirred for approximately 12 hours at about 20° C. to about 25° C. during which time a color change from dark purple to light green was observed. The reaction mixture was transferred into 75 mL of cold (about 0° C.) pentane, and a light green solid precipitated. The precipitate was filtered, washed with 4×20 mL of cold pentane, and dried under vacuum to afford (IMesH$_2$) (C$_7$H$_{10}$N$_2$)$_2$(Cl)$_2$Ru=CHPh 10 as a light green powder (1.9 gram, 99% yield).

$^1$H NMR (500 MHz, CD$_2$Cl$_2$): δ19.10 (s, 1H, CHPh), 8.18 (d, 2H, pyridine CH, J$_{HH}$=6.5 Hz), 7.64 (d, 2H, ortho CH, J$_{HH}$=7.5 Hz), 7.48 (t, 11H, para CH, J$_{HH}$=7.0 Hz), 7.38 (d, 2H, pyridine CH, J$_{HH}$=6.5 Hz), 7.08 (t, 2H, meta CH, J$_{HH}$=7.5 Hz), 7.00 (br. s, 2H, Mes CH), 6.77 (br. s, 2H, Mes CH), 6.49 (d, 2H, pyridine CH, J$_{HH}$=6.0 Hz), 6.15 (d, 2H, pyridine CH, J$_{HH}$=7.0 Hz), 4.07 (br. d, 4H, NCH$_2$CH$_2$N), 2.98 (s, 6H, pyridine CH$_3$), 2.88 (s, 6H, pyridine CH$_3$), 2.61–2.21 (multiple peaks, 18H, Mes CH$_3$).

Polymerization Example

A 75 gram mass of DCPD (containing about 24% trimerized DCPD) was polymerized using (IMesH$_2$)(C$_7$H$_{10}$N$_2$)$_2$(Cl)$_2$Ru=CHPh=0.0141 grams at a DCPD:Ru ratio of (about 30,000:1) at a starting temperature of about 24.2° C. Result: Time to reach maximum temperature (T$_{max}$)=389 seconds. T$_{max}$=175.3° C.

Synthesis of (IMesH$_2$)(C$_{10}$H$_8$N$_2$)(Cl)$_2$Ru=CHPh

Complex 1 (2.0 grams) was dissolved in toluene (10 mL), and 2,2'-bipyridine (0.74 grams, 2 mol equivalents) was added. The reaction flask was purged with argon and the reaction mixture was stirred for approximately 12 hours at about 20° C. to about 25° C. during which time a color change from dark purple to brown-red was observed. The reaction mixture was transferred into 75 mL of cold (about 0° C.) pentane, and an brown-red solid precipitated. The precipitate was filtered, washed with 4×20 mL of cold pentane, and dried under vacuum to afford (IMesH$_2$) (C$_{10}$H$_8$N$_2$)(Cl)$_2$Ru=CHPh 11 as a brown-red powder (0.7 gram, 41% yield).

Synthesis Of (IMeSH$_{12}$)(C$_6$H$_{15}$NO)$_2$(Cl)$_2$Ru=CHPh

Complex 1 (2.0 grams) was dissolved in toluene (10 mL), and 2-pyridinecarboxaldehyde (1.01 grams, 4 mol equivalents) was added. The reaction flask was purged with argon and the reaction mixture was stirred for approximately 12 hours at about 20° C. to about 25° C. during which time a color change from dark purple to dark blue was observed. The reaction mixture was transferred into 75 mL of cold (about 0° C.) pentane, and a dark blue solid precipitated. The precipitate was filtered, washed with 4×20 mL of cold pentane, and dried under vacuum to afford (IMesH$_2$) (C$_6$H$_5$NO)$_2$(Cl)$_2$Ru=CHPh 12 as a dark blue powder (1.3 gram, 70% yield).

Synthesis of (IMesH$_2$)(C$_{11}$H$_9$N)$_2$(Cl)$_2$Ru=CHPh

Complex 1 (2.0 grams) was dissolved in toluene (10 mL), and 4-phenylpyridine (1.50 grams, 4 mol equivalents) was added. The reaction flask was purged with argon and the reaction mixture was stirred for approximately 12 hours at about 20° C. to about 25° C. during which time a color change from dark purple to dark green was observed. The reaction mixture was transferred into 75 mL of cold (about 0° C.) pentane, and a dark green solid precipitated. The precipitate was filtered, washed with 4×20 mL of cold pentane, and dried under vacuum to afford (IMesH$_2$)

$(C_{11}H_9N)_2(Cl)_2Ru$=CHPh 13 as a dark green powder (2.0 grams, 97% yield).

$^1$H NMR (500 MHz, $CD_2Cl_2$): δ19.23 (s, 1H, CHPh), 8.74 (br. s, 2H, pyridine), 7.91 (br. s, 2H, pyridine), 7.70–7.08 (multiple peaks, 19H, ortho CH, para CH, meta CH, pyridine), 6.93 (br. S, 2H, Mes CH) 6.79 (br. s, 2H, Mes CH), 4.05 (br. s, 4H, $NCH_2CH_2N$), 2.62–2.29 (multiple peaks, 18H, Mes $CH_3$).

Polymerization Example

A 75 gram mass of DCPD (containing about 24% trimerized DCPD) was polymerized using $(IMesH_2)(C_{11}H_9N)_2(Cl)_2Ru$=CHPh=0.0153 grams at a DCPD:Ru ratio of (about 30,000:1) at a starting temperature of about 13.4° C.

Result

Time to reach maximum temperature ($T_{max}$)=145 seconds. $T_{max}$=202.2° C. Glass transition temperature measured by thermal mechanical analysis (TMA)=168° C. Percent residual monomer (toluene extraction at room temperature)=1.17%.

Synthesis of $(IMesH_2)(C_{18}H_{12}N_2)_2(Cl)_2Ru$=CHPh

Complex 1 (2.0 grams) was dissolved in toluene (10 mL), and 2,2'-biquinoline (1.21 grams, 2 mol equivalents) was added. The reaction flask was purged with argon and the reaction mixture was stirred for approximately 12 hours at about 20° C. to about 25° C. during which time a slight color change from dark purple to brown-purple was observed. The reaction mixture was transferred into 75 mL of cold (about 0° C.) pentane, and a brown-purple solid precipitated. The precipitate was filtered, washed with 4×20 mL of cold pentane, and dried under vacuum to afford $(IMesH_2)(C_{18}H_{12}N_2)_2(Cl)_2Ru$=CHPh 14 as a brown-purple powder (1.8 gram, 93% yield).

Synthesis of $(IMesH_2)(C_5H_{15}N)_2(Cl)_2Ru$=CHPh

Complex 1 (1.1 g, 1.3 mmol) was dissolved in toluene, and pyridine (110 mL) was added. The reaction was stirred for 10 min during which time a color change from pink to bright green was observed. The reaction mixture was cannula transferred into 75 mL of cold (about 0° C.) pentane, and a green solid precipitated. The precipitate was filtered, washed with 4×20 mL of pentane, and dried under vacuum to afford $(IMesH_2)(C_5H_5N)_2(Cl)_2Ru$=CHPh as a green powder (0.75 g, 80% yield). Samples for elemental analysis were prepared by recrystallization from $C_6H_6$/pentane followed by drying under vacuum. These samples analyze as the monopyridine adduct $(IMesH_2)(C_5H_5N)(Cl)_2Ru$=CHPh, probably due to loss of pyridine under vacuum.

$^1$H NMR ($C_6H_6$): δ19.67 (s, 1H, CHPh), 8.84 (br. S, 2H, pyridine), 8.39 (br. s, 2H, pyridine), 8.07 (d, 2H, ortho CH, $J_{HH}$=8 Hz), 7.15 (t, 1H, para CH, $J_{HH}$=7 Hz), 6.83–6.04 (br multiple peaks, 9H, pyridine, and Mes CH), 3.37 (br d, 4H, $CH_2CH_2$), 2.79 (br s, 6H, Mes $CH_3$), 2.45 (br s, 6H, Mes $CH_3$), 2.04 (br s, 6H, Mes $CH_3$).

$^{13}C\{^1H\}$NMR ($C_6D_6$): δ314.90 (m, Ru=CHPh), 219.10 (s, Ru—$C(N)_2$), 152.94, 150.84, 139.92, 138.38, 136.87, 135.99, 134.97, 131.10, 130.11, 129.88, 128.69, 123.38, 51.98, 51.37, 21.39, 20.96, 19.32. Anal. Calcd for $C_{33}H_{37}N_3Cl_2Ru$: C, 61.20; H, 5.76; N, 6.49. Found: C, 61.25; H, 5.76; N, 6.58.

Polymerization Example

A 75 gram mass of DCPD (containing about 24% trimerized DCPD) was polymerized using $(IMesH_2)(C_5H_5N)_2(Cl)_2Ru$=CHPh=0.0127 grams at a DCPD:Ru ratio of (about 30,000:1) at a starting temperature of about 12.1° C.

Result: Time to reach maximum temperature ($T_{max}$)=173 seconds. $T_{max}$=201.9° C. Glass transition temperature measured by thermal mechanical analysis (TMA)=164° C. Percent residual monomer (toluene extraction at room temperature)=1.05%.

Polymerization Example

A 50 gram mass of hexylnorbornene was polymerized using $(IMesH_2)(C_5H_5N)_2(Cl)_2Ru$=CHPh=0.0068 grams at a $H_xN$:Ru ratio of (about 30,000:1) at a starting temperature of about 12.2° C.

Result

Time to reach maximum temperature ($T_{max}$)=99 seconds. $T_{max}$=140.7° C.

Synthesis of $(PCp_3)(C_{12}H_8N_2)(Cl)_2Ru$=CH—CH=C$(CH_3)_2$

Complex 2 (2.0 grams) was dissolved in toluene (10 mL), and 1,10-phenanthroline (1.01 grams, 2 mol equivalents) was added. The reaction flask was purged with argon and the reaction mixture was stirred for approximately 12 hours at about 20° C. to about 25° C. during which time a color change from dark purple to red-brown was observed. The reaction mixture was transferred into 75 mL of cold (about 0° C.) pentane, and a red-brown solid precipitated. The precipitate was filtered, washed with 4×20 mL of cold pentane, and dried under vacuum to afford $(PCp_3)(C_{12}H_8N_2)(Cl)_2Ru$=CH—CH=C$(CH_3)_2$ 15 as an red-brown powder (1.8 gram, 98% yield).

Synthesis of $(PCp_3)(C_5H_4BrN)_2(Cl)_2Ru$=CH—CH=C$(CH_3)_2$

Complex 2 (2.0 grams) was dissolved in toluene (10 mL), and 3-bromopyridine (1.76 grams, 4 mol equivalents) was added. The reaction flask was purged with argon and the reaction mixture was stirred for approximately 12 hours at about 20° C. to about 25° C. during which time a color change from dark purple to green was observed. The reaction mixture was transferred into 75 mL of cold (about 0° C.) pentane, and a green solid precipitated. The precipitate was filtered, washed with 4×20 mL of cold pentane, and dried under vacuum to afford $(PCp_3)(C_5H_4BrN)_2(Cl)_2Ru$=CH—CH=C$(CH_3)_2$ 16 as an green powder (0.2 gram, 10% yield).

Synthesis of $(PCp_3)(C_5H_5N)_2(Cl)_2Ru$=CH—CH=C$(CH_3)_2$

Complex 2 (2.0 grams) was dissolved in toluene (10 mL), and pyridine (0.88 grams, 4 mol equivalents) was added. The reaction flask was purged with argon and the reaction mixture was stirred for approximately 12 hours at about 20° C. to about 25° C. during which time a color change from dark purple to green was observed. The reaction mixture was transferred into 75 mL of cold (about 0° C.) pentane, and a green solid precipitated. The precipitate was filtered, washed with 4×20 mL of cold pentane, and dried under vacuum to afford $(PCp_3)(C_5H_5N)_2(Cl)_2Ru$=CH—CH=C$(CH_3)_2$ 17 as a green powder (0.6 gram, 34% yield).

Synthesis of $(PCp_3)(C_6H_7N)_2(Cl)_2Ru$=CH—CH=C$(CH_3)_2$

Complex 2 (2.0 grams) was dissolved in toluene (10 mL), and 4-methylpyridine (1.04 grams, 4 mol equivalents) was added. The reaction flask was purged with argon and the reaction mixture was stirred for approximately 12 hours at about 20° C. to about 25° C. during which time a color change from dark purple to light green was observed. The reaction mixture was transferred into 75 mL of cold (about 0° C.) pentane, and a light green solid precipitated. The precipitate was filtered, washed with 4×20 mL of cold pentane, and dried under vacuum to afford $(PCp_3)(C_6H_7N)_2(Cl)_2Ru$=CH—CH=C$(CH_3)_2$ 18 as a light green powder (1.4 gram, 75% yield).

Synthesis of $(PCy_3)(C_{12}H_8N_2)(Cl)_2Ru=CH-CH=C(CH_3)_2$

Complex 3 (2.0 grams) was dissolved in toluene (10 mL), and 1,10-phenanthroline (0.91 grams, 2 mol equivalents) was added. The reaction flask was purged with argon and the reaction mixture was stirred for approximately 12 hours at about 20° C. to about 25° C. during which time a color change from dark purple to orange-brown was observed. The reaction mixture was transferred into 75 mL of cold (about 0° C.) pentane, and an orange-brown solid precipitated. The precipitate was filtered, washed with 4×20 mL of cold pentane, and dried under vacuum to afford $(PCy_3)(C_{12}H_9N_2)(Cl)_2Ru=CH-CH=C(CH_3)_2$ 19 as an orange-brown powder (1.7 gram, 97% yield).

Synthesis of $(PCy_3)(C_5H_4BrN)_2(Cl)_2Ru=CH-CH=C(CH_3)_2$

Complex 3 (2.0 grams) was dissolved in toluene (10 mL), and 3-bromopyridine (1.58 grams, 4 mol equivalents) was added. The reaction flask was purged with argon and the reaction mixture was stirred for approximately 12 hours at about 20° C. to about 25° C. during which time no dramatic color change from dark purple was observed. The reaction mixture was transferred into 75 mL of cold (about 0° C.) pentane, and a purple solid precipitated. The precipitate was filtered, washed with 4×20 mL of cold pentane, and dried under vacuum to afford $(PCy_3)(C_5H_4BrN)_2(Cl)_2Ru=CH-CH=C(CH_3)_2$ 20 as a purple powder (1.4 gram, 67% yield).

Synthesis of $(PCy_3)(C_{11}H_9N)_2(Cl)_2Ru=CH-CH=C(CH_3)_2$

Complex 3 (2.0 grams) was dissolved in toluene (10 mL), and 4-phenylpyridine (1.55 grams, 4 mol equivalents) was added. The reaction flask was purged with argon and the reaction mixture was stirred for approximately 12 hours at about 20° C. to about 25° C. during which time a color change from dark purple to brown was observed. The reaction mixture was transferred into 75 mL of cold (about 0° C.) pentane, and a brown solid precipitated. The precipitate was filtered, washed with 4×20 mL of cold pentane, and dried under vacuum to afford $(PCy_3)(C_{11}H_9N)_2(Cl)_2Ru=CH-CH=C(CH_3)_2$ 21 as a brown powder (1.6 gram, 77% yield).

Synthesis of $(PCy_3)(C_6H_7N)_2(Cl)_2Ru=CH-CH=C(CH_3)_2$

Complex 3 (2.0 grams) was dissolved in toluene (10 mL), and 4-methylpyridine (0.93 grams, 4 mol equivalents) was added. The reaction flask was purged with argon and the reaction mixture was stirred for approximately 12 hours at about 20° C. to about 25° C. during which time a color change from dark purple to green was observed. The reaction mixture was transferred into 75 mL of cold (about 0° C.) pentane, and a green solid precipitated. The precipitate was filtered, washed with 4×20 mL of cold pentane, and dried under vacuum to afford $(PCy_3)(C_6H_7N)_2(Cl)_2Ru=CH-CH=C(CH_3)_2$ 22 as a green powder (1.6 gram, 91% yield).

Synthesis of $(PCy_3)(C_5H_5N)_2(Cl)_2Ru=CH-CH=C(CH_3)_2$

Complex 3 (2.0 grams) was dissolved in toluene (10 mL), and pyridine (0.79 grams, 4 mol equivalents) was added. The reaction flask was purged with argon and the reaction mixture was stirred for approximately 12 hours at about 20° C. to about 25° C. during which time a color change from dark purple to light green was observed. The reaction mixture was transferred into 75 mL of cold (about 0° C.) pentane, and a light green solid precipitated. The precipitate was filtered, washed with 4×20 mL of cold pentane, and dried under vacuum to afford $(PCy_3)(C_5H_5N)_2(Cl)_2Ru=CH-CH=C(CH_3)_2$ 23 as a light green powder (1.4 gram, 83% yield).

Polymerization Example

A 75 gram mass of DCPD (containing about 24% trimerized DCPD) was polymerized using $(PCy_3)(C_5H_1N)_2(Cl)_2Ru=CH-CH=C(CH_3)_2$=0.0237 grams at a DCPD:Ru ratio of (about 15,000:1) at a starting temperature of about 52.2° C.

Result

Time to reach maximum temperature ($T_{max}$)=1166 seconds. $T_{max}$=60.2° C.

Polymerization Example

A 75 gram mass of DCPD (containing about 24% trimerized DCPD) was polymerized using $(PCy_3)(C_5H_5N)_2(Cl)_2Ru=CH-CH=C(CH_3)_2$=0.0237 grams in the presence of $sImesHCCl_3$=0.0297 grams at a DCPD:Ru:sImesHCCl₃ ratio of (about 15,000:1:2) at a starting temperature of about 49.4° C. Result: Time to reach maximum temperature ($T_{max}$)=715 seconds. $T_{max}$=173.3° C.

Synthesis of $(IMesH_2)(C_{11}H_9N)_2(Cl)_2Ru=CH-CH=C(CH_3)_2$

Complex 4 (1.5 grams) was dissolved in toluene (10 mL), and 4-phenylpyridine (1.13 grams, 4 mol equivalents) was added. The reaction flask was purged with argon and the reaction mixture was stirred for approximately 2 hours at about 20° C. to about 25° C. during which time a color change from brown to green was observed. The reaction mixture was transferred into 75 mL of cold (about 0° C.) pentane, and a green solid precipitated. The precipitate was filtered, washed with 4×20 mL of cold pentane, and dried under vacuum to afford $(IMesH_2)(C_{11}H_9N)_2(Cl)_2Ru=CH-CH=C(CH_3)_2$ 24 as a green powder (0.9 gram, 58% yield).

Synthesis of $(IMesH_2)(C_9H_{12}N_2)_2(Cl)_2Ru=CH-CH=C(CH_3)_2$

Complex 4 (1.5 grams) was dissolved in toluene (10 mL), and 4-pyrrolidinopyridine (1.08 grams, 4 mol equivalents) was added. The reaction flask was purged with argon and the reaction mixture was stirred for approximately 2 hours at about 20° C. to about 25° C. during which time a color change from brown to green was observed. The reaction mixture was transferred into 75 mL of cold (about 0° C.) pentane, and a green solid precipitated. The precipitate was filtered, washed with 4×20 mL of cold pentane, and dried under vacuum to afford $(IMesH_2)(C_9H_{12}N_2)_2(Cl)_2Ru=CH-CH=C(CH_3)_2$ 25 as a green powder (1.0 gram, 65% yield).

$^1$H NMR (300 MHz, $CD_2Cl_2$): δ19.05 (d, 1H, CH-CH=C(CH₃)₂, $J_{HH}$=11 Hz), 8.14 (br. s, 2H, pyridine CH), 7.69 (d, 1H, CH-CH=C(CH₃)₂, $J_{HH}$=11 Hz), 7.36 (d, 2H, pyridine CH, $J_{HH}$=6.0 Hz), 7.04 (s, 2H, Mes CH), 6.81 (s, 2H, Mes CH), 6.36 (br. s, 2H, pyridine CH), 6.12 (d, 2H, pyridine CH, $J_{HH}$=6.0 Hz), 4.06 (m. d, 4H, NCH₂CH₂N), 3.29 (br. s, 4H, pyrrolidine CH₂), 3.23 (br. s, 4H, pyrrolidine CH₂), 2.55–2.12 (multiple peaks, 18H, Mes CH₃), 2.02 (br. s, 4H, pyrrolidine CH₂), 1.97 (br. s, 4H, pyrrolidine CH₂), 1.10 (s, 3H, CH-CH=C(CH₃)₂), 1.08 (s, 3H, CH-CH=C(CH₃)₂).

Polymerization Example

A 75 gram mass of DCPD (containing about 24% trimerized DCPD) was polymerized using $(IMesH_2)(C_9H_{12}N_2)_2(Cl)_2Ru=CH-CH=C(CH_3)_2$=0.0147 grams at a DCPD:Ru ratio of (about 30,000:1) at a starting temperature of about 24.7° C. Result: Time to reach maximum temperature ($T_{max}$)=181 seconds. $T_{max}$=200.9° C. Glass transition temperature measured by thermal mechanical analysis (TMA)=

144° C. Percent residual monomer (toluene extraction at room temperature)=3.93%.

Synthesis of (IMesH$_2$)(C$_{10}$H$_8$N$_2$)$_2$(Cl)$_2$Ru=CH—CH=C(CH$_3$)$_2$

Complex 4 (1.5 grams) was dissolved in toluene (10 mL), and 4,4'-bipyridine (0.57 grams, 2 mol equivalents) was added. The reaction flask was purged with argon and the reaction mixture was stirred for approximately 2 hours at about 20° C. to about 25° C. during which time no dramatic color change from brown was observed. The reaction mixture was transferred into 75 mL of cold (about 0° C.) pentane, and a brown solid precipitated. The precipitate was filtered, washed with 4×20 mL of cold pentane, and dried under vacuum to afford (IMesH$_2$)(C$_{10}$H$_8$N$_2$)$_2$(Cl)$_2$Ru=CH—CH=C(CH$_3$)$_2$ 26 as a brown powder (1.0 gram, 64% yield).

Synthesis of (IMesH$_2$)(C$_7$H$_{10}$N$_2$)$_2$(Cl)$_2$Ru=CH—CH=C(CH$_3$)$_2$

Complex 4 (1.5 grams) was dissolved in toluene (10 mL), and 4-dimethylaminopyridine (0.89 grams, 4 mol equivalents) was added. The reaction flask was purged with argon and the reaction mixture was stirred for approximately 2 hours at about 20° C. to about 25° C. during which time a color change from brown to green was observed. The reaction mixture was transferred into 75 mL of cold (about 0° C.) pentane, and a green solid precipitated. The precipitate was filtered, washed with 4×20 mL of cold pentane, and dried under vacuum to afford (IMesH$_2$)(C$_7$H$_{10}$N$_2$)$_2$(Cl)$_2$Ru=CH—CH=C(CH$_3$)$_2$ 27 as a green powder (0.9 gram, 63% yield).

$^1$H NMR (500 MHz, CD$_2$Cl$_2$): δ19.10 (d, 1H, CH—CH=C(CH$_3$)$_2$, J$_{HH}$=11.5 Hz,), 8.18 (br. s, 2H, pyridine CH), 7.69 (d, 1H, CH—CH=C(CH$_3$)$_2$, J$_{HH}$=11.5 Hz), 7.41 (br. s, 2H, Mes CH), 6.49 (br. s, 2H, pyridine CH), 6.24 (br. s, 2H, Mes CH), 4.06 (br. m, 4H, NCH$_2$CH$_2$N), 2.99 (s, 6H, pyridine CH$_3$), 2.59 (s, 6H, pyridine CH$_3$), 2.36–2.12 (multiple peaks, 18H, Mes CH$_3$), 1.07 (s, 3H, CH—CH=C(CH$_3$)$_2$), 1.06 (s, 3H, CH—CH=C(CH$_3$)$_2$).

Polymerization Example

A 75 gram mass of DCPD (containing about 24% trimerized DCPD) was polymerized using (IMesH$_2$)(C$_7$H$_{10}$N$_2$)$_2$(Cl)$_2$Ru=CH—CH=C(CH$_3$)$_2$=0.0138 grams at a DCPD:Ru ratio of (about 30,000:1) at a starting temperature of about 24.2° C. Result: Time to reach maximum temperature (T$_{max}$)=200 seconds. T$_{max}$=200.9° C. Glass transition temperature measured by thermal mechanical analysis (TMA)= 145° C. Percent residual monomer (toluene extraction at room temperature) 4.57%.

Polymerization Example

A 50 gram mass of hexylnorbornene was polymerized using (IMesH$_2$)(C$_7$H$_{10}$N$_2$)$_2$(Cl)$_2$Ru=CH—CH=C(CH$_3$)$_2$= 0.0074 grams at a H$_x$N:Ru ratio of (about 30,000:1) at a starting temperature of about 16.2° C.

Result

Time to reach maximum temperature (T$_{max}$)=182 seconds. T$_{max}$=141.7° C.

Synthesis of (IMesH$_2$)(C$_5$H$_5$N)$_2$(Cl)$_2$Ru=CH—CH=C(CH$_3$)$_2$

Complex 4 (0.5 grams) was dissolved in toluene (10 mL), and pyridine (10 mL) was added. The reaction flask was purged with argon and the reaction mixture was stirred for approximately 12 hours at about 20° C. to about 25° C. during which time a color change from brown to browngreen was observed. The reaction mixture was transferred into 75 mL of cold (about 0° C.) pentane, and a green solid precipitated. The precipitate was filtered, washed with 4×20 mL of cold pentane, and dried under vacuum to afford 28 (IMesH$_2$)(C$_5$H$_5$N)$_2$(Cl)$_2$Ru=CH—CH=C(CH$_3$)$_2$ as green crystals (0.2 gram, 47% yield).

$^1$H NMR (300 MHz, CD$_2$Cl$_2$): δ19.19 (d, 1H, Ru=CH—CH=C(CH$_3$)$_2$, J$_{HH}$=10.8 Hz), 8.60–6.85 (multiple peaks, 15H, pyridine, Mes CH, Ru=CH—CH=C(CH$_3$)$_2$, 4.07 (m, 4H, NCH$_2$CH$_2$N), 2.58–2.27 (multiple peaks, 12H, Mes CH$_3$), 2.31 (s, 3H, Mes CH$_3$), 2.19 (s, 3H, Mes CH$_3$), 1.09 (s, 3H, CH—CH=C(CH$_3$)$_2$), 1.08 (s, 3H, CH—CH=C(CH$_3$)$_2$).

Polymerization Example

A 75 gram mass of DCPD (containing about 24% trimerized DCPD) was polymerized using (IMesH$_2$)(C$_5$H$_5$N)$_2$(Cl)$_2$Ru=CH—CH=C(CH$_3$)$_2$=0.0123 grams at a DCPD:Ru ratio of (about 30,000:1) at a starting temperature of about 12.5° C. Result: Time to reach maximum temperature (T$_{max}$)=129 seconds. T$_{max}$=197.1° C. Glass transition temperature measured by thermal mechanical analysis (TMA)= 157° C. Percent residual monomer (toluene extraction at room temperature)=2.13%.

Synthesis of (IMesH$_2$)(C$_5$H$_5$N)$_2$(Cl)$_2$Ru=CHPh (31)

Complex 1 (4.0 g, 4.7 mmol) was dissolved in toluene (10 mL), and pyridine (30 mL, 0.37 mol) was added. The reaction was stirred for 10 min during which time a color change from red to bright green was observed. The reaction mixture was cannula transferred into 100 mL of cold (−10° C.) pentane, and a green solid precipitated. The precipitate was filtered, washed with 4×50 mL of pentane, and dried under vacuum to afford 31 as a green powder (2.9 g, 85% yield). Samples for elemental analysis were prepared by recrystallization from C$_6$H$_6$/pentane followed by drying under vacuum. These samples analyze as the monopyridine adduct (IMesH$_2$)(C$_5$H$_5$N)(Cl)$_2$Ru=CHPh, probably due to loss of pyridine under vacuum. $^1$H NMR (C$_6$D$_6$): δ19.67 (s, 1H, CHPh), 8.84 (br. s, 2H, pyridine), 8.39 (br. s, 2H, pyrdine), 8.07 (d, 2H, ortho CH, J$_{HH}$=8 Hz), 7.15 (t, 1H, para CH, J$_{HH}$=7 Hz), 6.83–6.04 (br. multiple peaks, 9H, pyridine, Mes CH), 3.37 (br. d, 4H, CH$_2$CH$_2$), 2.79 (br. s, 6H, Mes CH$_3$), 2.45 (br. s, 6H, Mes CH$_3$), 2.04 (br. s, 6H, Mes CH$_3$). C{$^1$H} NMR (C$_6$D$_6$): δ314.90 (m, Ru=CHPh), 219.10 (s, Ru—C(N)$_2$), 152.94, 150.84, 139.92, 138.38, 136.87, 135.99, 134.97, 131.10, 130.11, 129.88, 128.69, 123.38, 51.98, 51.37, 21.39, 20.96, 19.32. Anal. Calcd for C$_{33}$H$_{37}$N$_3$Cl$_2$Ru: C, 61.20; H, 5.76; N, 6.49. Found: C, 61.25; H, 5.76; N, 6.58.

Representatative Synthesis of a Phosphine Complex: IMesH$_2$)(PPh$_3$)(Cl)$_2$Ru=CHPh (41)

Complex 31 (150 mg, 0.21 mmol) and PPh$_3$ (76 mg, 0.28 mmol) were combined in benzene (10 mL) and stirred for 10 min. The solvent was removed under vacuum, and the resulting brown residue was washed with 4×20 mL of pentane and dried in vacuo. Complex 41 was obtained as a brownish powder (125 mg, 73% yield). $^{31}$P {$^1$H} NMR (C$_6$D$_6$): δ37.7 (s). $^1$H NMR (C$_7$D$_8$): δ19.60 (s, $^1$H, Ru=CHPh), 7.70 (d, 2H, ortho CH, J$_{HH}$=8 Hz), 7.29–6.71 (multiple peaks, 20H, PPh$_3$, para CH, meta CH, and Mes CH), 6.27 (s, 2H, Mes CH), 3.39 (m, 4H, CH$_2$CH$_2$), 2.74 (s, 6H, ortho CH$_3$), 2.34 (s, 6H, ortho CH$_3$), 2.23 (s, 3H, para CH$_3$), 1.91 (s, 3H, para CH$_3$). $^{13}$C{$^1$H} NMR (C$_6$D$_6$): δ305.34 (m, Ru—CHPh), 219.57 (d, Ru—C(N)$_2$, J$_{CP}$=92 Hz), 151.69 (d, J$_{CP}$=4 Hz), 139.68, 138.35, 138.10, 138.97, 137.78, 135.89, 135.21, 135.13, 131.96, 131.65, 131.36, 130.47, 129.83, 129.59 (d, J$_{CP}$=2 Hz), 129.15, 128.92, 128.68, 128.00, 52.11 (d, J$_{CP}$=4 Hz), 51.44 (d, J$_{CP}$=2 Hz), 21.67, 21.35, 21.04, 19.21. Anal. Calcd for C$_{46}$H$_{47}$N$_2$Cl$_2$PRu: C, 66.50; H, 5.70; N, 3.37. Found: C, 66.82; H, 5.76; N, 3.29.

Synthesis of (IMesH$_2$)(O$^t$Bu)$_2$Ru=CHPh (42)

Complex 31 (7.5 mg, 0.010 mmol) and KO$^t$Bu (3 mg, 0.027 mmol) were combined in C$_6$D$_6$ (0.6 mL) in an NMR tube under nitrogen. The reaction mixture was allowed to stand for 15–20 min, during which time a color change from green to dark red was was observed, and NMR spectra were recorded after 30 min. $^1$H NMR (C$_6$D$_6$): δ16.56 (s, 1H, Ru=CHPh), 7.63 (d, 2H, ortho CH, J$_{HH}$=7 Hz), 7.2–7.1 (multiple peaks, 3H, meta CH and ortho CH), 6.97 (s, 4H, Mes CH), 3.43 (s, 4H CH$_2$CH$_2$), 2.59 (s, 12H, ortho CH$_3$), 2.29 (s, 6H, para CH$_3$), 1.18 (s, 18H, $^t$Bu).

Synthesis of Tp(IMesH$_2$)(Cl)Ru=CHPh (43)

KTp (87 mg, 0.34 mmol) and complex 31 (125 mg, 0.17 mmol) were combined in CH$_2$Cl$_2$ (10 mL) and stirred for 1 hour. Pentane (20 mL) was added to precipitate the salts, and the reaction was stirred for an additional 30 min and then cannula filtered. The resulting bright green solution was concentrated, and the solid residue was washed with pentane (2×10 mL) and methanol (2×10 mL) and dried under vacuum to afford 43 (84 mg, 66% yield) as an analytically pure green powder. $^1$H NMR (CD$_2$Cl$_2$): δ18.73 (s, 1H, Ru=CHPh), 7.87 (d, 1H, Tp, J$_{HH}$=2.4 Hz), 7.41 (d, 1H, Tp, J$_{HH}$=2.1 Hz), 7.35–7.30 (multiple peaks, 3H, Tp and para CH), 7.08 (d, 1 h, Tp, J$_{HH}$=1.5 Hz), 6.82 (br. s, 5H, Mes CH, ortho CH and meta CH), 6.24 (br. s, 3H, Mes CH), 6.16 (t, 1H, Tp, J$_{HH}$=1.8 Hz) 5.95 (d, 1H, Tp, J$_{HH}$=1.5 Hz), 5.69 (t, 1H, Tp, J$_{HH}$=2.4 Hz), 5.50 (t, 1H, Tp, J$_{HH}$=1.8 Hz), 3.77 (br. d, 4H, CH$_2$CH$_2$), 2.91–0.893 (br. multiple peaks, 18H, ortho CH$_3$, para CH$_3$). $^{13}$C{$^1$H} (CD$_2$Cl$_2$): δ324.29 (m, Ru=CHPh), 220.57 (s, Ru—C(N)$_2$), 151.50, 146.08, 145.39, 142.07, 137.94, 136.57, 134.41, 133.18, 130.60 (br), 129.55, 127.98, 106.41, 105.19, 104.51, 53.77 (br), 21.26, 20.32 (br). Anal. Calcd for C$_{37}$H$_{42}$N$_8$ClBRu: C, 59.56; H, 5.67; N, 15.02. Found: C, 59.20; H, 5.67; N, 14.72.

Kinetics of the Reaction of 1 with C$_5$D$_5$N

In a cuvette fitted with a rubber septum, a solution of 1 (0.88 mM) in toluene (1.6 mL) was prepared. This solution was allowed to thermally equilibrate in the Uv-vis spectrometer at 20° C. Neat pyridine-d5 (25–100 μL) was added via microsyringe, and the reaction kinetics was followed by monitoring the disappearance of starting material (502 nm). For each run, the data were collected over 5 half-lives and were fitted to a first-order expoential. Typical R$^2$ values for the exponential curve fits were greater than 0.999.

X-ray Crystal Structure of 31

Crystal, intensity collection, and refinement details were summarized in Table 1. The selected crystal was mounted on a glass fiber with Paratone-N oil and transferred to a Bruker SMART 1000 CCD area detector equipped with a Crystal Logic CL24 low-temperature device. Data were collected with ω-scans at seven φ values and subsequently processed with SAINT. No absorption or decay corrections were applied. SHELXTL was used to solve (by direct methods and subsequent difference Fourier maps) and to refine (full-matrix least-squares on F$^2$) the structure. There are two molecules in the asymmetric unit. All non-hydrogen atoms were refined anisotropically; the hydrogen atoms were placed at calculated positions with U$_{iso}$ values based on the U$_{eq}$ of the attached atom. Pertinent bond lengths and angles for one molecule are presented in Table 2.

Synthesis of (IMes)(C$_5$H$_5$N)$_2$(Cl)$_2$Ru=CHPh

In a nitrogen filled glovebox, 0.120 g (0.142 mmol) of (IMes)(PCy$_3$)Cl$_2$Ru=CHPh were dissolved in 1 mL of pyridine (large excess). The solution, which turned green immediately, was stirred at room temperature for 30 minutes. Then 20 mL of hexanes was added, and the flask was stored at −10° C. overnight. The supernatant was decanted from the green precipitate. The precipitate was washed twice with 20 mL hexanes and dried under vacuum to obtain 0.080 g (78% yield) of the bright green product (IMes)(py)$_2$Cl$_2$Ru=CHPh.

$^1$H NMR (499.852 MHz, CD$_2$Cl$_2$): δ19.41 (s, 1H, CHPh), 8.74 (d, 2H, J=7.5 Hz), 7.96 (d, 2H, J=8.5 Hz), 7.70 (d, 2H, J=12.5 Hz), 7.55 (t, 1H, J=12.5 Hz), 7.44 (t, 1H, J=12 Hz), 7.33 (t, 1H, J=12 Hz), 7.06 (m, 3H), 7.05 (s, 2H), 6.83 (m, 1H), 6.79 (s, 6H), 2.28 (s, 6H, para CH$_3$ on Mes), 2.22 (br s, 12H, ortho CH$_3$ on Mes).

Characterization of (PCy$_3$)(C$_5$H$_5$N)$_2$(Cl)$_2$Ru=CH—CH=C(CH$_3$)$_2$ $^1$H NMR (499.852 MHz, C$_6$D$_6$): δ20.18 (overlapping dd, 1H, J=10.3 Hz, Ru=CH), 9.14 (br s, 4H, pyridine), 8.07 (d, 1H, J=11.5 Hz, —CH=), 6.68 (br s, 3H, pyridine), 6.43 (br m, 3H, pyridine), 2.54 (qt, 3H, J=11.5 Hz, PCy$_3$), 2.27 (d, 6H, J=11.5 Hz, PCy3), 1.91 (qt, 6H, J=12 Hz, PCy$_3$), 1.78 (d, 6H, J=10.5 Hz, PCy$_3$), 1.62 (m, 4H, PCy$_3$), 1.26 (s, 3H, CH$_3$), 1.23 (m, 8H, PCy$_3$), 0.75 (s, 3H, CH$_3$). $^{31}$P{$^1$H} NMR (121.392 MHz, C$_6$D$_6$): δ37.17 (s).

Observation of (Ph$_3$Tri)(C$_7$H$_{10}$N$_2$)$_2$(Cl)$_2$Ru=CH—CH=C(CH$_3$)$_2$ 0.020 g of (Ph$_3$Tri)(PCy$_3$)(Cl)$_2$Ru=CH—CH=C(CH$_3$)$_2$, 0.020 g of 4-dimethylaminopyridine (excess), and 0.060 mL of CD$_2$Cl$_2$ were added to a screw-cap NMR tube. The $^1$H NMR spectrum after 2 hours at room temperature showed complete conversion to the desired product (Ph$_3$Tri)(C$_7$H$_{10}$N$_2$)$_2$(Cl)$_2$Ru=CH—CH=C(CH$_3$)$_2$.

$^1$H NMR (499.852 MHz, C$_6$D$_6$): δ18.57 (d, 1H, J=13 Hz, Ru=CH), 8.53 (d, J=8 Hz), 7.84 (d, J=6.5 Hz), 7.73–6.84 (multiplets), 6.26 (d, J=7 Hz), 6.09 (m), 6.04 (d, J=10.5 Hz), 6.01 (d, J=10.5 Hz), 5.42 (d, J=10.5 Hz), 5.38 (d, J=17.5 Hz), 3.22 (s), 3.01 (s), 2.99 (s), 1.73 (s), 1.23 (s).

What is claimed is:

1. A compound of the formula:

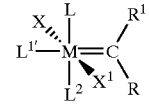

wherein

M is ruthenium or osmium;

X and X$^1$ are the same or different and are each independently any anionic ligand;

L, L$^{1'}$, and L$^2$ are the same or different and are each independently any neutral electron donor ligand; wherein at least one of L, L$^{1'}$, and L$^2$ is an N-heterocyclic carbene ligand;

R and R$^1$ are the same or different and are each independently hydrogen or a substituted or unsubstituted substituent selected from the group consisting of C$_1$–C$_{20}$ alkyl, C$_2$–C$_{20}$ alkenyl, C$_2$–C$_{20}$ alkynyl, aryl, C$_1$–C$_{20}$ carboxylate, C$_1$–C$_{20}$ alkoxy, C$_2$–C$_{20}$ alkenyloxy, C$_2$–C$_{20}$ alkynyloxy, aryloxy, C$_2$–C$_{20}$ alkoxycarbonyl, C$_1$–C$_{20}$ alkylthio, C$_1$–C$_{20}$ alkylsulfonyl and C$_1$–C$_{20}$ alkylsulfinyl.

2. The compound of claim 1 wherein at least one of the R and R$^1$ substituent group is substituted with one or more moieties selected from the group consisting of C$_1$–C$_{10}$ alkyl, C$_1$–C$_{10}$ alkoxy, and aryl, and wherein the moiety is substituted or unsubstituted.

3. The compound of claim 2 wherein the moiety is substituted with one or more groups selected from the group consisting of halogen, a C$_1$–C$_5$ alkyl, C$_1$–C$_5$ alkoxy, and phenyl.

4. The compound of claim 1 wherein R is hydrogen and $R^1$ is selected from the group consisting of $C_1$–$C_{20}$ alkyl, $C_2$–$C_{20}$ alkenyl, and aryl.

5. The compound of claim 4 wherein $R^1$ is phenyl or vinyl.

6. The compound of claim 1 wherein X and $X^1$ are each independently hydrogen, halide, or selected from the group consisting of $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, and $C_1$–$C_{20}$ alkylsulfinyl, wherein X and $X^1$ is each independently substituted or unsubstituted.

7. The compound of claim 6 wherein at least one of X and $X^1$ is substituted with one or more moieties selected from the group consisting of $C_1$–$C_{10}$ alkyl, $C_1$–$C_{10}$ alkoxy, and aryl, wherein the moiety is substituted or unsubstituted.

8. The compound of claim 7 wherein the moiety is substituted with one or more groups selected from the group consisting of halogen, $C_1$–$C_5$ alkyl, $C_1$–$C_5$ alkoxy, and phenyl.

9. The compound of claim 1 wherein X and $X^1$ are each independently selected from the group consisting of halide, benzoate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate.

10. The compound of claim 9 wherein X and $X^1$ are each independently selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate.

11. The compound of claim 1 wherein L, $L^{1'}$ and $L^2$ are each independently selected from the group consisting of a monodentate, bidentate and tetradentate neutral electron donor ligand.

12. The compound of claim 11 wherein L, $L^{1'}$ and L are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, thioether, N-heterocyclic carbene ligand and any derivatives therefrom.

13. The compound of claim 1 wherein both $L^{1'}$ and $L^2$ are either the same or different N-heterocyclic carbene ligands.

14. The compound of claim 1 wherein the N-heterocyclic carbene ligand is selected from the group consisting of:

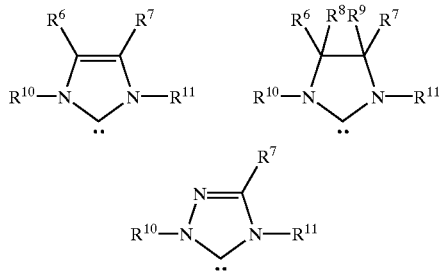

wherein R, $R^1$, $R^6$, $R^7$, $R^8$, $R^9$, $R^{10}$, and $R^{11}$ are each independently hydrogen or a substituted or unsubstituted substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl.

15. The compound of claim 1 wherein L is an N-heterocyclic carbene ligand, and $L^{1'}$ and $L^2$ are each heterocyclic ligands.

16. The compound of claim 15 wherein at least one of $L^1$ and $L^2$ is aromatic.

17. The compound of claim 15 wherein $L^{1'}$ and $L^2$ together form a bidenatate ligand.

18. The compound of claim 1 at least one of $L^{1'}$ and $L^2$ is a unsubstituted or substituted heteroarene selected from the group consisting of furan, thiophene, pyrrole, pyridine, bipyridine, picolylimine, gamma-pyran, gamma-thiopyran, phenanthroline, pyrimidine, bipyrimidine, pyrazine, indole, coumarone, thionaphthene, carbazole, dibenzofuran, dibenzothiophene, pyrazole, imidazole, benzimidazole, oxazole, thiazole, dithiazole, isoxazole, isothiazole, quinoline, bisquinoline, isoquinoline, bisisoquinoline, acridine, chromene, phenazine, phenoxazine, phenothiazine, triazine, thianthrene, purine, bisimidazole and bisoxazole.

19. The compound of claim 18 wherein at least one of $L^{1'}$ and $L^2$ is a substituted or unsubstituted pyridine or a substituted or unsubstituted pyridine derivative.

20. The compound of claim 18 wherein the substituted or unsubstituted heteroarene is selected from the group consisting of:

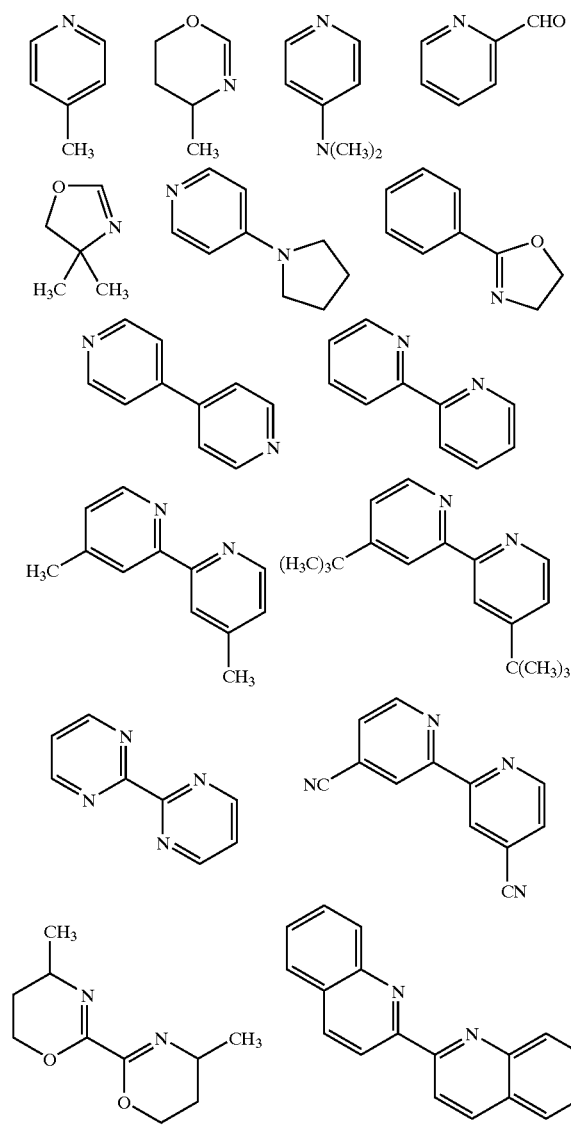

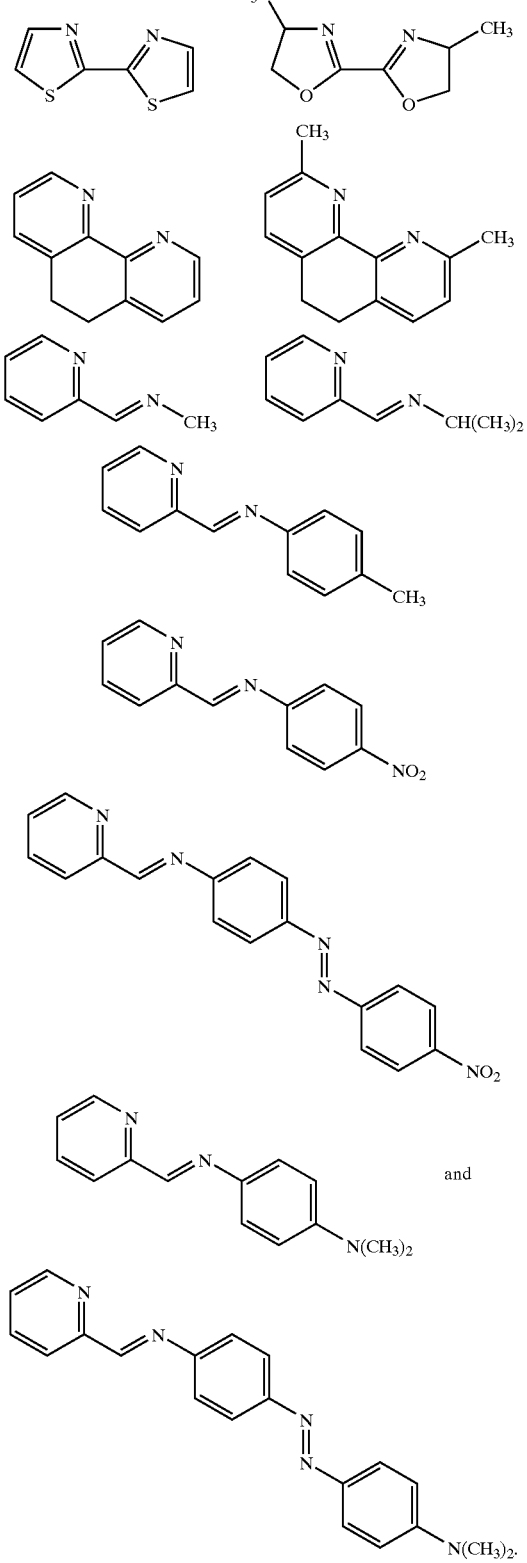

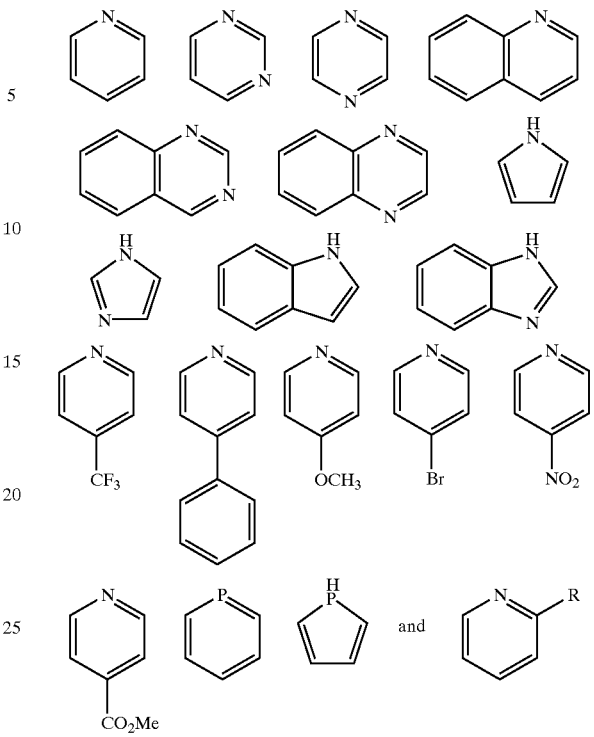

wherein R is selected from the group consisting of $C_1$–$C_{20}$ alkyl, aryl, ether, amide, halide, nitro, ester, and pyridyl.

22. A compound of the formula:

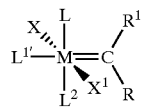

wherein

M is ruthenium;

X and $X^1$ are each independently selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate;

L is an N-heterocyclic carbene ligand;

$L^{1'}$ and $L^2$ are the same or different and are each a substituted or unsubstituted heteroarene, and wherein $L^{1'}$ and $L^2$ may be joined;

R is hydrogen and $R^1$ is selected from the group consisting of $C_1$–$C_{20}$ alkyl, $C_2$–$C_{20}$ alkenyl, and aryl.

23. The compound of claim 22 wherein X and $X^1$ are each Cl, L is (IMesH$_2$), $L^{1'}$ and $L^2$ are each independently a pyridine or pyridine derivative; R is hydrogen and $R^1$ is phenyl or vinyl.

21. The compound of claim 1 wherein at least one of $L^{1'}$ and $L^2$ is a unsubstituted or substituted heterocycle selected from the group consisting of:

24. A compound selected from the group consisting of:
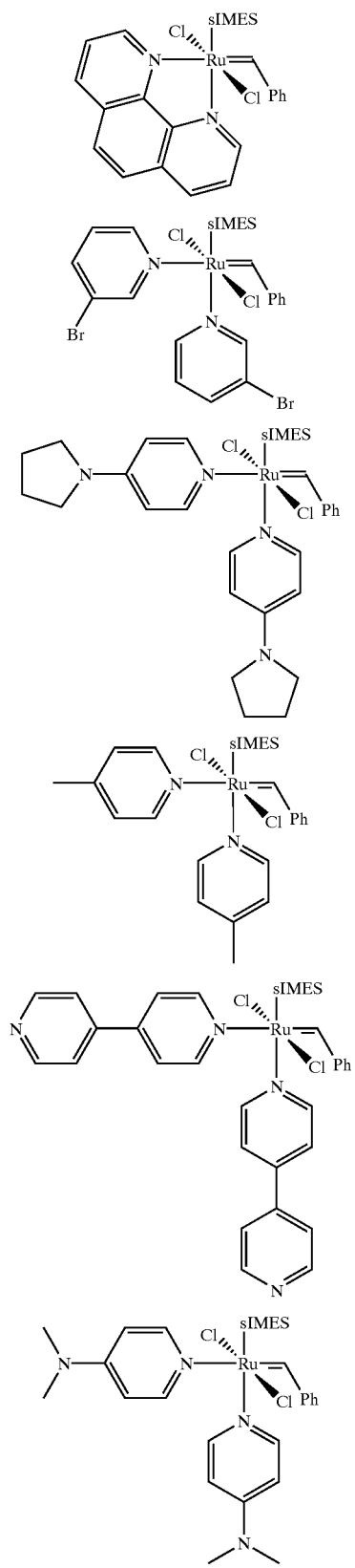
-continued
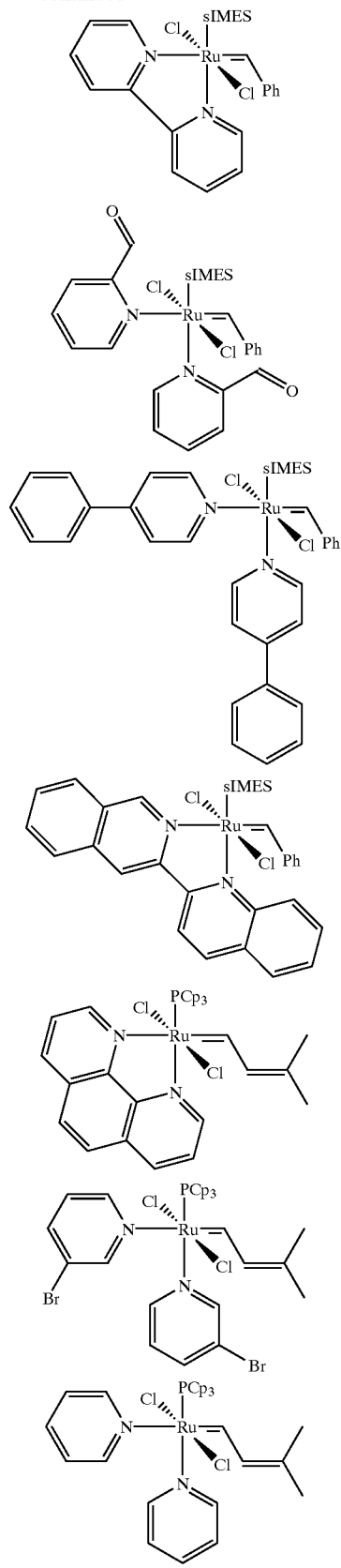

-continued
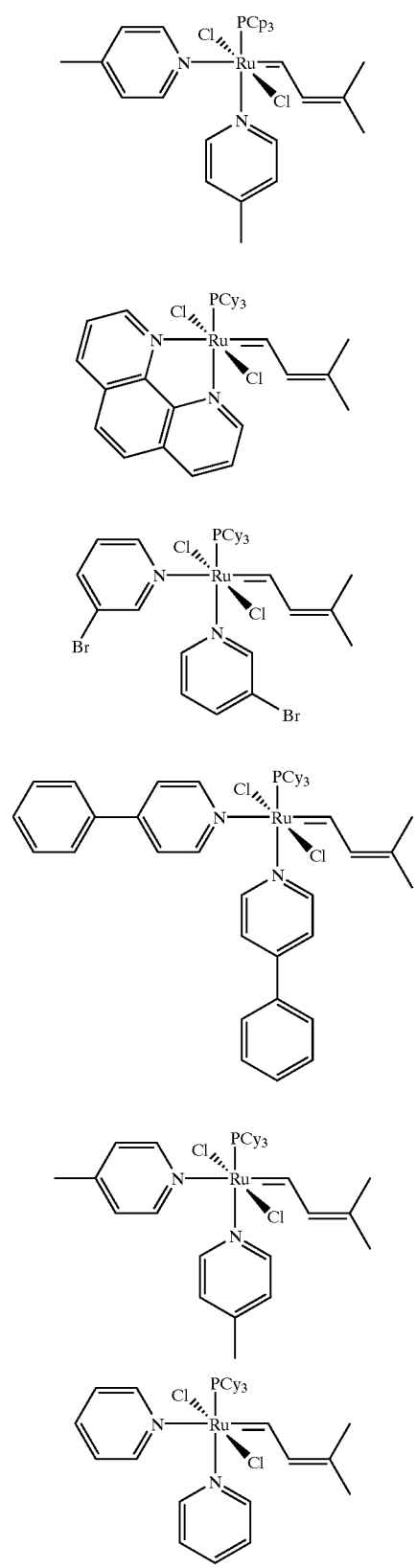
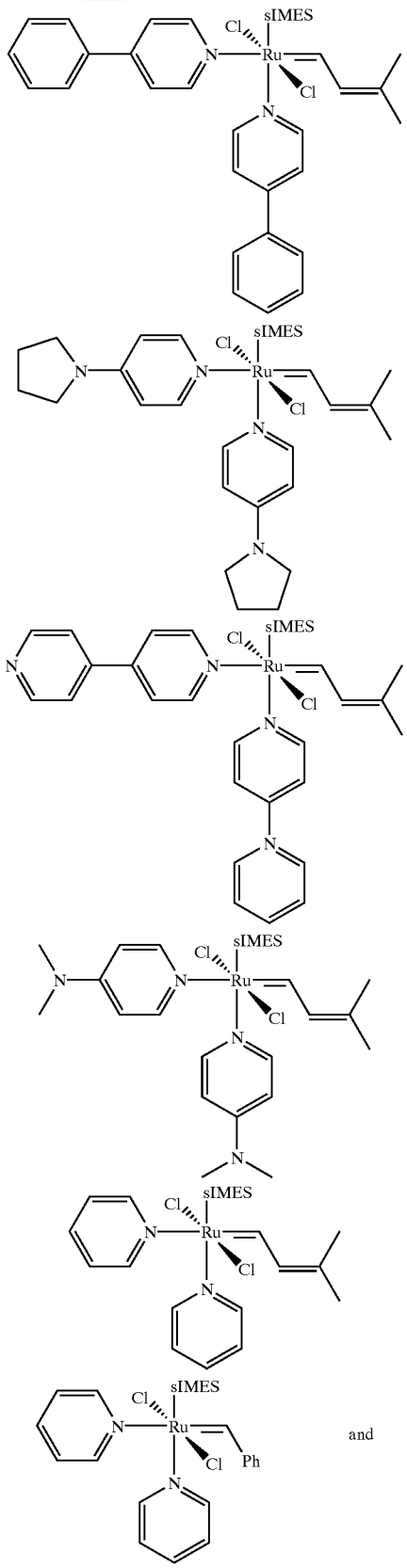
and

-continued

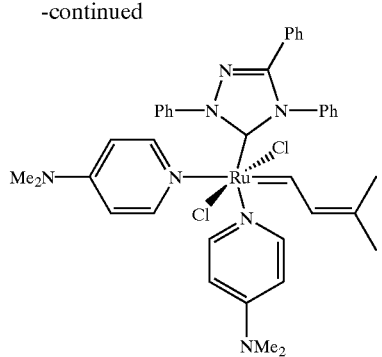

wherein sIMES is

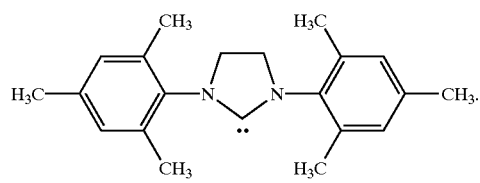

25. A compound of the formula:

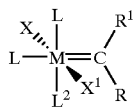

wherein

M is ruthenium or osmium;

X and $X^1$ are the same or different and are each independently any anionic ligand;

L, $L^{1'}$, and $L^2$ are the same or different and are each independently any neutral electron donor ligand;

R is hydrogen or a substituted or unsubstituted substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl;

$R^1$ is substituted or unsubstituted $C_2$–$C_{20}$ alkenyl.

26. The compound of claim 25 wherein $R^1$ is substituted or unsubstituted vinyl.

* * * * *